United States Patent [19]
Brant et al.

[11] Patent Number: 5,871,919
[45] Date of Patent: Feb. 16, 1999

[54] METHOD OF IDENTIFYING AGENTS THAT AFFECT HUMAN NHE3

[76] Inventors: Steven R. Brant, 8240 Brattle Rd., Baltimore, Md. 21208; C.H. Chris Yun, 659 Budleigh Cir., Timonium, Md. 21093; Mark Donowitz, 4308 Greenway, Baltimore, Md. 21218; Chung-Ming Tse, 8027 York Rd., Apt. C8, Baltimore, Md. 21204

[21] Appl. No.: 677,734

[22] Filed: Jul. 10, 1996

Related U.S. Application Data

[60] Provisional application No. 60/001,061 Jul. 11, 1995.

[51] Int. Cl.$^6$ .............................. C12Q 1/68; C12N 15/12; C07K 14/435
[52] U.S. Cl. ............................ 435/6; 435/69.1; 536/23.5; 530/350
[58] Field of Search .......................... 530/350; 435/69.1, 435/6, 7.1; 436/501; 536/23.5

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis et al. | 435/91 |
| 5,359,045 | 10/1994 | Soubrier et al. | 536/23.2 |

OTHER PUBLICATIONS

Chung–Ming Tse et al., Molecular Properties, Kinetics and Regulation of Mammalian Na+/H+ Exchangers, Cell Physiol. Biochem. 4:282–300 (1994).

W.A. Hoogerwerf et al., Message Distribution of Three Na+/H+ Exchangers Along the Rabbit Lleal Crypt–Villus Axis and Demonstration that an Epithelial Isoform, NHE2, is Present in Lleal Brush Border Membrane, Intestinal Disorders A239 (Apr. 1994).

Crescence Bookstein et al., Na+/H+ Exchangers, NHE–1 and NHE–3, of Rat Intestine, J. Clin. Invest. 93:106–113 (1994).

S.A. Levine et al., Kinetics and Regulation of Three Cloned Mammalian Na+/H+ Exchangers Stably Expressed in a Fribroblast Cell Line, The Journal of Biological Chemistry 268:25527–25535 (1993).

Daniel Biemesderfer et al., NHE3: a Na+/H+ exchanger isoform of renal brush border, American Journal of Physiology: Renal, Fluid and Electrolyte Physiology 34:F736–F742 (1993).

John Orlowski, Heterologous Expression and Functional Properties of Amiloride High Affinity (NHE–1) and Low Affinity (NHE–3) Isoforms of the Rat Na/H Exchanger, The Journal of Biological Chemistry 268:16369–16377 (1993).

C.H. Chris Yun et al., LEU143 In the Putative Fourth Membrane Spanning Domain is Critical for Amiloride Inhibition of an Epithelial Na+/H+ Exchanger Isoform (NHE–2), Biochemical and Biophysical Research Communications 193:532–539 (1993).

Chung–Ming Tse et al., Cloning and Expression of a Rabbit cDNA Encoding a Serum–activated Ethylisopropylamiloride–resistant Epithelial Na+/H+ Exchanger Isoform (NHE–2), The Journal of Biological Chemistry 268:11917–11924 (1993).

Laurent Counillon et al., A point mutation of the Na+/H+ exchanger gene (NHE1) and amplification of the mutated allele confer amiloride resistance upon chronic acidosis, Proc. Natl. Acad. Sci. 90:4508–4512 (1993).

C.H. Chris Yun et al., Glucocorticoid Stimulation of Lleal Na+ Absorptive Cell Brush Border Na+/H+ Exchange and Association with an Increase in Message for NHE–3, an Epithelial Na+/H+ Exchanger Isoform, The Journal of Biological Chemistry 268:206–211 (1993).

Steven R. Brant et al., Physical and Genetic Mapping of a Human Apical Epithelial Na+/H+ Exchanger (NHE3) Isoform to Chromosome 5p15.3, Genomics 15:668–672 (1993).

W. Richard McCombie et al., Rapid and reliable fluorescent cycle sequencing of double–stranded templates, DNA sequence: J. DNA Sequencing and Mapping 2:289–296 (1992).

Zafar Zamir et al., Sodium Transport in Human Intestinal Basolateral Membrane Vesicles, Gastroenterology 103:1817–1822 (1992).

Franck Borgese et al., Cloning and expression of a cAMP–activated Na+/H+ exchanger: Evidence that the cytoplasmic domain mediates hormonal regulation, Proc. Nat'l. Acad. Sci. 89:6765–6769 (1992).

S. Harguindey et al., The Na+/H+ Antiporter in Oncology in the Light of the Spontaneous Regression of Cancer and Cell Metabolism, Medical Hypotheses 39:229–237 (1992).

John Orlowski et al., Molecular Cloning of Putative Members of the Na/H Exchanger Gene Family, The Journal of Biological Chemistry, 267:9331–9339 (1992).

Shigeo Wakabayashi et al., The Na+/H+ antiporter cytoplasmic domain mediates growth factor signals and controls "H+–sensing", Proc. Natl. Acad. Sci. 89:2424–2428 (1992).

L. Domenjoud et al., On the expression of protamine genes in the testis of man and other manimals, Androlocia, 23:333–337 (1991).

C. Ming Tse et al., Molecular cloning and expression of a cDNA encoding the rabbit Lleal villus cell basolateral membrane Na+/H+ exchanger, The EMBO Journal 10:1957–1967 (1991).

(List continued on next page.)

*Primary Examiner*—John Ulm
*Assistant Examiner*—Christine Saoud
*Attorney, Agent, or Firm*—Finnegan, Henderson, Farabow, Garrett and Dunner

[57] ABSTRACT

The present invention teaches a method of identifying agents that affect NHE3. Specifically, these methods comprise the steps of obtaining DNA encoding all or a portion of human NHE3, introducing that DNA into a recipient host cell whereby the host cell can perform Na+/H+ exchange, applying agents to the host cell, and assessing whether the agents affect Na+/H+ exchange.

4 Claims, 9 Drawing Sheets

OTHER PUBLICATIONS

R. Tyler Miller et al., Structure of the 5'–Flanking Regulatory Region and Gene for the Human Growth Factor–activatable Na/H Exchanger NHE–1, The Journal of Biological Chemistry 266:10813–10819 (1991).

Sari Acra et al., Increased Na+–H+ Exchange in Jejunal Brush Border Membrane Vesicles of Spontaneously Hypertensive Rats, Gastroenterology 101:430–436 (1991).

Richard P. Lifton et al., Cloning of the Human Genomic Amiloride–Sensitive Na+/H+ Antiporter Gene, Identification of Genetic Polymorphisms, and Localization on the Genetic Map of Chromosome 1p, Genomics 7:131–135 (1990).

Gabriel A. Morduchawicz et al., Increased Na+/H+ antiport activity in the renal brush border memebrane of SHR, Kidney International 36:576–581 (1989).

Claude Sardet et al., Molecular Cloning, Primary Structure, and Expression of the Human Growth Factor–Activatable Na+/H+ Antiporter, Cell 56:271–280 (1989).

J.S. Tung et al., PCR Amplification of Specific Sequences from a cDNA Library, PCR Technology: Principles and Applications for DNA Amplification, 99–104.

J.G. Kleinman et al., Na+ and H+ transport in human jejunal brush–border membrane vesicles, Am. J. Physiol. 255:G206–G211 (1988).

Louis Simchowitz et al., Intracellular Acidification–induced Alkali Metal Cation/H+ Exchange in Human Neutrophils, J. Gen. Physiol. 90:737–762 (1987).

Marilyn Kozak, An analysis of 5'–noncoding sequences from 699 vertebrate messenger RNAs, Nucleic Acids Research, 15:8125–8132 (1987).

Pamela C. Yelick et al., Mouse Protamine 2 is Synthesized as a Precursor whereas Mouse Protamine 1 is Not, Molecular and Cellular Biology 7:2173–2179 (1987).

Lloyd M. Smith et al., Fluorescence detection in automated DNA sequence analysis, Nature 321:674–678 (1986).

Rex L. Mahnensmith et al., The Plasma Membrane Sodium–Hydrogen Exchanger and its Role in Physiological and Pathophysiological Processes, Circulation Research 56:773–788 (1985).

Roy Knickelbein et al., Sodium and chloride transport across rabbit ileal brush border. Evidence for CI–HCO$_3$ exchange and mechanism of coupling, Am. J. Physiol. 249:G236–G245 (1985).

I.W. Booth et al., Defective Jejunal Brush–Border Na+/H+ Exchange: A Cause of Congenital Secretory Diarrhoea, The Lancet 1:1066–1069 (1985).

Roy Knickelbein et al., Sodium and chloride transport across rabbit ileal brush border. L. Evidence for Na–H exchange, Am. J. Physiol. 245:G504–G510 (1983).

Peter S. Aronson, Mechanisms of active H+ secretion in the proximal tubule, Am. J. Physiol. 245:F657–F659 (1983).

J. Michael Freiberg et al. Glucocorticoids increase the Na+–H+ exchange and decrease the Na+ gradient–dependent phosphate–uptake systems in renal brush border membrane vesicles, Proc. Natl. Acad. Sci. 79:4932–4936 (1982).

F. Sanger et al., DNA sequencing with chain–terminating inhibitors, Biochemistry, 74:5463–5467 (1977).

Steven R. Brant et al, "Physical and Genetic Mapping of a Human Apical Epithelia Na$^+$/H$^+$ Exchanger (NHE3) Isoform to Chromosome 5p15.3," Genomics, 15:668–672 (1993).

Steven R. Brant et al., "Cloning, tissue distribution, and functional analysis of the human Na$^+$/H$^+$ exchanger isoform, NHE3," American J. Physiol., vol. 269, No. 1, pp. C198–C206.

Chung–Ming Tse et al., "Cloning and Sequencing of a Rabbit cDNA Encoding an Intestinal and Kidney–specific Na$^+$/H$^+$ Exchanger Isoform (NHE–3)," Journal of Biological Chemistry, vol. 267, No. 13, pp. 9340–9346 (1992).

Mark Donowitz et al., "Regulation of Mammilian Small Intestinal Electrolyte Secretion," Physiology of the Gastrointestinal Tract, 2nd Ed., Raven Press, New York, pp. 1351–1388 (1987).

H. M. Berschneider et al., "Altered intestinal chloride transport in cystic fibrosis," FASEB J. Vol. 2, pp. 2625–2629 (1988).

Chung–Ming Tse et al., "Structure/Function Studies of the Epithelial Isoforms of the Mammalian Na$^+$/H$^+$ Exchanger Gene Family," The Journal of Membrane Biology, vol. 135, pp. 93–108 (1993).

Chung–Ming Tse et al., "Functional characteristics of a cloned epithelial Na$^+$/H$^+$ exchanger (NHE3): Resistance to amiloride and inhibition by protein kinase C,"Proc. Natl. Acad. Sci., USA, vol. 90, pp. 9110–9114 (Oct. 1993).

Richard P. Rood et al., "Regulation of Small Intestine Na$^+$ Absorption by Protein Kinases: Implications for Therapy of Diarrheal Diseases," Viewpoints on Digestive Diseases, vol. 22, No. 2, pp. 1–6 (1990).

```
RABBIT NHE3   -36  ATGCGCGTCGGGCCCCGGCGCTGA  -13
RAT    NHE3   -33  ATGCGTGTCGGCTCCTGGAGCTGA  -10
                   ****  ****  **  **  *****
```

```
                                                         GCAGGCGGCA    -1
       ATGTGGGGACTCGGGGCCCGGGGCCCCGACCGGGGGGCTGCTGCTGGCGCTGGCG          54
  1    M  W  G  L  G  A  R  G  P  D  R  G  L  L  L  A  L  A
       CTGGGCGGGCTGGCGCGGGCCGGGGGCGTCGAGGTGGAGCCCGGCGGCGCGCAC           108
 19    L  G  G  L  A  R  A  G  G  V  E  V  E  P  G  G  A  H
       GGCGAGAGCGGGGGCTTCCAGGTGGTCACCTTCGAGTGGGCCCACGTGCAGGAT           162
 37    G  E  S  G  G  F  Q  V  V  T  F  E  W  A  H  V  Q  D
       CCCTACGTCATCGCGCTCTGGATCCTCGTGGCCAGCTTGGCCAAGATCGGGTTC           216
 55    P  Y  V  I  A  L  W  I  L  V  A  S  L  A  K  I  G  F
       CACCTGTCCCACAAGGTCACCAGCGTGGTTCCCGAGAGCGCCCTGCTCATCGTG           270
 73    H  L  S  H  K  V  T  S  V  V  P  E  S  A  L  L  I  V
       CTGGGCCTGGTGCTGGGCGGCATCGTCTGGGCGGCCGACCACATCGCGTCCTTC           324
 91    L  G  L  V  L  G  G  I  V  W  A  A  D  H  I  A  S  F
       ACACTGACGCCCACCGTCTTCTTCTTCTACCTGCTGCCCCCCATCGTGCTGGAC           378
109    T  L  T  P  T  V  F  F  F  Y  L  L  P  P  I  V  L  D
       GCCGGCTACTTCATGCCCAACCGCCTCTTCTTCGGCAACCTGGGGACCATCCTG           432
127    A  G  Y  F  M  P  N  R  L  F  F  G  N  L  G  T  I  L
       TTGTACGCCGTCGTGGGTACCGTGTGGAACGCGGCCACCACCGGGCTGTCCCTC           486
145    L  Y  A  V  V  G  T  V  W  N  A  A  T  T  G  L  S  L
       TACGGCGTCTTCCTCAGTGGGCTCATGGGCGACCTGCAGATTGGCTGCTGGAC           540
163    Y  G  V  F  L  S  G  L  M  G  D  L  Q  I  G  L  L  D
       TTCCTCCTGTTTGGCAGCCTCATGGCGGCTGTGGACCCGGTGGCCGTCCTGGCC           594
181    F  L  L  F  G  S  L  M  A  A  V  D  P  V  A  V  L  A
       GTGTTTGAGGAGGTCCATGTCAACGAGGTCCTGTTCATCATCGTCTTCGGGGAG           648
199    V  F  E  E  V  H  V  N  E  V  L  F  I  I  V  F  G  E
       TCGCTGCTGAACGACGCAGTCACCGTGGTTCTGTACAATGTGTTTGAATCTTTC           702
217    S  L  L  N  D  A  V  T  V  V  L  Y  N  V  F  E  S  F
       GTGGCGCTGGGAGGTGACAACGTGACTGGCGTGGACTGCGTGAAGGGCATAGTG           756
235    V  A  L  G  G  D  N  V  T  G  V  D  C  V  K  G  I  V
       TCCTTCTTCGTGGTGAGCCTGGGGGGCACGCTGGTGGGGGTGGTCTTCGCCTTC           810
253    S  F  F  V  V  S  L  G  G  T  L  V  G  V  V  F  A  F
       CTGCTGTCGCTGGTGACGCGCTTCACCAAGCATGTGCGTATCATCGAGCCCGGC           864
271    L  L  S  L  V  T  R  F  T  K  H  V  R  I  I  E  P  G
       TTCGTGTTCATCATCTCCTACCTGTCCTACCTGACGTCCGAGATGCTGTCGCTG           918
289    F  V  F  I  I  S  Y  L  S  Y  L  T  S  E  M  L  S  L
       TCGGCCATCCTCGCCATCACCTTCTGTGGCATCTGCTGTCAGAAGTATGTGAAG           972
307    S  A  I  L  A  I  T  F  C  G  I  C  C  Q  K  Y  V  K
       GCCAACATCTCGGAGCAGTCGGCCACCACCGTGCGCTACACCATGAAGATGCTG          1026
325    A  N  I  S  E  Q  S  A  T  T  V  R  Y  T  M  K  M  L
       GCCAGCAGCGCCGAGACCATCATCTTCATGTTCCTGGGTATCTCGGCCGTGAAC          1080
343    A  S  S  A  E  T  I  I  F  M  F  L  G  I  S  A  V  N
       CCGTTCATCTGGACCTGGAACACGGCCTTCGTGCTCCTGACGCTGGTCTTCATC          1134
361    P  F  I  W  T  W  N  T  A  F  V  L  L  T  L  V  F  I
       TCCGTGTACCGGGCCATCGGTGTGGTCCTGCAGACCTGGCTTCTGAACCGCTAC          1188
379    S  V  Y  R  A  I  G  V  V  L  Q  T  W  L  L  N  R  Y
       CGCATGGTGCAGCTGGAGCCCATTGACCAGGTGGTCCTGTCCTACGGGGGCCTG          1242
397    R  M  V  Q  L  E  P  I  D  Q  V  V  L  S  Y  G  G  L
       CGCGGGGCCGTGGCCTTTGCCCTGGTGGTGCTTCTGGATGGAGACAAGGTCAAG          1296
415    R  G  A  V  A  F  A  L  V  V  L  L  D  G  D  K  V  K
       GAGAAGAACCTGTTCGTCAGCACCACCATCATCGTAGTGTTCTTCACCGTCATC          1350
433    E  K  N  L  F  V  S  T  T  I  I  V  V  F  F  T  V  I
```

*FIG. 3A*

```
     TTCCAGGGCCTGACCATCAAGCCTCTGGTGCAGTGGCTGAAGGTGAAGAGGAGC 1404
451   F  Q  G  L  T  I  K  P  L  V  Q  W  L  K  V  K  R  S
     GAGCACCGGGAACCTCGGCTCAACGAGAAGCTGCACGGCCGCGCTTTCGACCAC 1458
469   E  H  R  E  P  R  L  N  E  K  L  H  G  R  A  F  D  H
     ATCCTCTCGGCCATCGAGGACATATCCGGACAGATCGGGCACAATTATCTCAGA 1512
487   I  L  S  A  I  E  D  I  S  G  Q  I  G  H  N  Y  L  R
     GACAAGTGGTCCCACTTCGACAGGAAGTTCCTCAGCAGGGTCCTCATGAGACGG 1566
505   D  K  W  S  H  F  D  R  K  F  L  S  R  V  L  M  R  R
     TCGGCCCAGAAGTCTCGAGACCGGATCCTGAATGTCTTCCACGAGCTGAACCTG 1620
523   S  A  Q  K  S  R  D  R  I  L  N  V  F  H  E  L  N  L
     AAGGATGCCATCAGCTACGTGGCTGAGGGAGAGCGCCGCGGGTCCCTGGCCTTC 1674
541   K  D  A  I  S  Y  V  A  E  G  E  R  R  G  S  L  A  F
     ATCCGCTCCCCCAGCACCGACAACGTGGTCAACGTGGACTTCACGCCACGATCG 1728
559   I  R  S  P  S  T  D  N  V  V  N  V  D  F  T  P  R  S
     TCCACCGTGGAGGCCTCTGTCTCCTACCTCCTGAGAGAAAATGTCAGCGCTGTC 1782
577   S  T  V  E  A  S  V  S  Y  L  L  R  E  N  V  S  A  V
     TGCCTGGACATGCAGTCTCTGGAGCAGCGACGGCGGAGCATCCGGGACGCGGAG 1836
595   C  L  D  M  Q  S  L  E  Q  R  R  R  S  I  R  D  A  E
     GACATGGTCACGCACCACACGCTACAGCAGTACCTGTACAAGCCGCGGCAGGAG 1890
613   D  M  V  T  H  H  T  L  Q  Q  Y  L  Y  K  P  R  Q  E
     TACAAGCATCTGTACAGCCGACACGAGCTCACGCCCACGGAGGACGAGAAACAG 1944
631   Y  K  H  L  Y  S  R  H  E  L  T  P  T  E  D  E  K  Q
     GACCGGGAAATCTTCCACAGGACCATGCGGAAGCGCCTGGAGTCCTTCAAGTCG 1998
649   D  R  E  I  F  H  R  T  M  R  K  R  L  E  S  F  K  S
     ACCAAGCTGGGGCTCAACCAGAACAAGAAGGCAGCCAAGCTGTACAAGCGGGAG 2052
667   T  K  L  G  L  N  Q  N  K  K  A  A  K  L  Y  K  R  E
     CGTGCCCAGAAGCGGAGAAACAGCAGCATCCCCAATGGGAAGCTGCCCATGGAG 2106
685   R  A  Q  K  R  R  N  S  S  I  P  N  G  K  L  P  M  E
     AGCCCTGCGCAGAATTTCACCATCAAGGAGAAAGACTTGGAACTTTCAGACACC 2160
703   S  P  A  Q  N  F  T  I  K  E  K  D  L  E  L  S  D  T
     GAGGAGCCCCCCAACTATGATGAGGAGATGAGTGGGGGGATCGAGTTCCTGGCT 2214
721   E  E  P  P  N  Y  D  E  E  M  S  G  G  I  E  F  L  A
     AGTGTCACCAAGGACACAGCGTCCGACTCCCCTGCAGGAATTGACAACCCTGTG 2268
739   S  V  T  K  D  T  A  S  D  S  P  A  G  I  D  N  P  V
     TTTTCTCCGGACGAGGCCCTGGACCGCAGCCTCCTGGCCAGGCTGCCGCCCTGG 2322
757   F  S  P  D  E  A  L  D  R  S  L  L  A  R  L  P  P  W
     CTGTCTCCCGGGGAGACGGTGGTCCCCTCGCAGAGGGCCCGCACGCAGATTCCC 2376
775   L  S  P  G  E  T  V  V  P  S  Q  R  A  R  T  Q  I  P
     TACTCTCCCGGCACCTTCCGCCGCCTGATGCCCTTCCGCCTCAGCAGCAAGTCC 2430
793   Y  S  P  G  T  F  R  R  L  M  P  F  R  L  S  S  K  S
     GTGGACTCCTTCCTGCAGGCAGACGGCCCCGAGGAGCGGCCCCCCGCCGCCCTC 2484
811   V  D  S  F  L  Q  A  D  G  P  E  E  R  P  P  A  A  L
     CCCGAGTCCACACACATGTGACACCGGCTCCGACACGCCGCTAACCGGCCGCTC 2538
829   P  E  S  T  H  M  *
     GTCCCCGCGCCACGGTCCGCCCACCGCCGCCGCCGC                    2574
```

FIG. 3B

```
                    m1
HUMNHE3  MWGLGARGPDRGLLLALALG--GLARAGGVEVEPGGAHGESGGFQVVTFEWAHVQDP   55
RATNHE3  MWH-PALGPGWKPLLALAVAVTSLRGVRGIEEEPNSG----GSFQIVTFKWHHVQDP    52
RABNHE3  MSGRGGCGPCWGLLLALVLALGALPWTQGAEQEH---HDEIQGFQIVTFKWHHVQDP    54
          *   **  ****  . *   * *         .  ** *** * *****
                 m2                        m3
HUMNHE3  YVIALWILVASLAKIGFHLSHKVTSVVPESALLIVLGLVLGGIVWAADHIASFTLTP   112
RATNHE3  YIIALWILVASLAKIVFHLSHKVTSVVPESALLIVLGLVLGGIVWAADHIASFTLTP   109
RABNHE3  YIIALWVLVASLAKIVFHLSHKVTSVVPESALLIVLGLVLGGIVLAADHIASFTLTP   111
         * **** ******* ***************************** **********
             m4                       m5
HUMNHE3  TVFFFYLLPPIVLDAGYFMPNRLFFGNLGTILLYAVVGTVWNAATTGLSLYGVFLSG   169
RATNHE3  TLFFFYLLPPIVLDAGYFMPNRLFFGNLGTILLYAVIGTIWNAATTGLSLYGVFLSG   166
RABNHE3  TVFFFYLLPPIVLDAGYFMPNRLFFSNLGSILLYAVVGTVWNAATTGLSLYGVFLSG   168
         * ********************** *** ****** ** *****************
                  m5a                             m5b
HUMNHE3  LMGDLQIGLLDFLLFGSLMAAVDPVAVLAVFEEVHVNEVLFIIVFGESLLNDAVTVV   226
RATNHE3  LMGELKIGLLDFLLFGSLIAAVDPVAVLAVFEEVHVNEVLFIIVFGESLLNDAVTVV   223
RABNHE3  IMGELKIGLLDFLLFGSLIAAVDPVAVLAVFEEVHVNEVLFIIVFGESLLNDAVTVV   225
          ** * *************  ************************************
                                  m6
HUMNHE3  LYNVFESFVALGGDNVTGVDCVKGIVSFFVVSLGGTLVGVVFAFLLSLVTRFTKHVR   283
RATNHE3  LYNVFESFVTLGGDAVTGVDCVKGIVSFFVVSLGGTLVGVIFAFLLSLVTRFTKHVR   280
RABNHE3  LYNVFQSFVTLGGDKVTGVDCVKGIVSFFVVSLGGTLVGVVFAFLLSLVTRFTKHVR   282
         ***** *** **** ************************ ****************
                                m7
HUMNHE3  IIEPGFVFIISYLSYLTSEMLSLSAILAITFCGICCQKYVKANISEQSATTVRYTMK   340
RATNHE3  IIEPGFVFVISYLSYLTSEMLSLSAILAITFCGICCQKYVKANISEQSATTVRYTMK   337
RABNHE3  VIEPGFVFIISYLSYLTSEMLSLSSILAITFCGICCQKYVKANISEQSATTVRYTMK   339
          ****** ***************  ********************************
                  m8                     M9
HUMNHE3  MLASSAETIIFMFLGISAVNPFIWTWNTAFVLLTLVFISVYRAIGVVLQTWLLNRYR   397
RATNHE3  MLASGAETIIFMFLGISAVDPVIWTWNTAFVLLTLVFISVYRAIGVVLQTWILNRYR   394
RABNEE3  MLASGAETIIFMFLGISAVDPLIWTWNTAFVRLTLLFVSVFRAIGVVLQTWLLNRYR   396
         **** ************** *  ******** * ** *  ********** ****
                                                    m10
HUMNHE3  MVQLEPIDQVVLSYGGLRGAVAFALVVLLDGDKVKEKNLFVSTTIIVVFFTVIFQGL   454
RATNHE3  MVQLETIDQVVMSYGGLRGAVAYALVVLLDEKKVKEKNLFVSTTLIVVFFTVIFQGL   451
RABNHE3  MVQLELIDQVVMSYGGLRGAVAFALVALLDGNKVKEKNLFVSTTIIVVFFTVIFQGL   453
         ***** *****.********* *** *** *************.************
```

*FIG. 4A*

```
HUMNHE3  TIKPLVQWLKVKRSEHREPRLNEKLHGRAFDHILSAIEDISGQIGHNYLRDKWSHFD  511
RATNHE3  TIKPLVQWLKVKRSEQREPKLNEKLHGRAFDHILSAIEDISGQIGHNYLRDKWSNFD  508
RABNHE3  TIKPLVQWLKVKRSEHREPKLNEKLHGRAFDHILSAIEDISGQIGHNYLRDKWANFD  510
         ************* *** ****************************** .**
                       +
HUMNHE3  RKFLSRVLMRRSAQKSRDRILNVFHELNLKDAISYVAEGERRGSLAFIRSPSTDNVV  568
RATNHE3  RKFLSKVLMRRSAQKSRDRILNVFHELNLKDAISYVAEGERRGSLAFIRSPSTDNMV  565
RABNHE3  RRFLSKLLMRQSAQKSRDRILNVFHELNLKDAISYVTEGERRGSLAFIRSPSTDNMV  567
         * *** .. *** ****************************. **************.*
              #                                    #
HUMNHE3  NVDF-TPRSSTVEASVSYLLRENVSAVCLDMQSLEQRRRSIRDAEDMVTHHTLQQYL  624
RATNHE3  NVDFSTPRPSTVEASVSYFLRENVSAVCLDMQSLEQRRRSIRDTEDMVTHHTLQQYL  622
RABNHE3  NVDFSTPRPSTVEASVSYLLRESASAVCLDMQSLEQRRRSVRDAEDVITHHTLQQYL  624
         **** *** ********* *** .****************.**.**..********
                   #       #  #
HUMNHE3  YKPRQEYKHLYSRHELTPTEDEKQDREIFHRTMRKRLESFKSTKLGLNQNKKAAKLY  681
RATNHE3  YKPRQEYKHLYSRHELTPNEDEKQDKEIFHRTMRKRLESFKSAKLGINQNKKAAKLY  679
RABNHE3  YKPRQEYKHLYSRHVLSPSEDEKQDKEIFHRTMRKRLESFKSAKLGLGQSKKATKHK  681
         ************** * ******.******************.***..*.***.*
                      #
HUMNHE3  K-RERAQKRRNSSIPNGKLPMESPAQNFTIKEKDLELSDTEEPPNY--DEEMSGGIE  735
RATNHE3  K-RERAQKRRNSSIPNGKLPMENLAHNFTIKEKDLELSEPEEATNY---EEISGGIE  732
RABNHE3  RERERAQKRRNSSVPNGKLPLDSPRYGLTLKERELELSDPEEAPDYYEAEKMSGGIE  738
         . ************.******. .    .. .** .*** .** ..* * .*****
                                                          #
HUMNHE3  FLASVTKDTASDSPAGIDNPVFSPDEALDRSLLARLPPWLSPGETVVPSQRARTQIP  792
RATNHE3  FLASVTKDVASDSGAGIDNPVFSPDEDLDPSILSRVPPWLSPGETVVPSQRARVQIP  789
RABNHE3  FLASVTKVSTSDSPAGIDNPVFSPDEDLAPSLLARVPPWLSPGEAVVPSQRARVQIP  795
         *******  *** *************.*..*..*.*********.********.***
                #
HUMNHE3  YSPGTFRRLMPFRLSSKSVDSFLQADGPEERPPAALPESTHM  834
RATNHE3  NSPSNFRRLTPFRLSNKSVDSFLQADGPEEQLQPASPESTHM  831
RABNHE3  YSPGNFRRLAPFRLSNKSVDSFLLAEDGAEH-----PESTHM  832
         .** .**** *****.******* *.*  .      ******
```

*FIG. 4B*

METHOD OF IDENTIFYING AGENTS THAT AFFECT HUMAN NHE3

This application claims benefit under 35 U.S.C. §119(e)(1) to provisional application Ser. No. 60/001,061 filed in the United States Patent and Trademark Office on 11 Jul., 1995.

BACKGROUND

The $Na^+/H^+$ exchangers, or antiporters, are plasma membrane transport proteins that exchange extracellular $Na^+$ for intracellular $H^+$ and are found in virtually all animals. In fact, all eukaryotic cells studied, including yeast, the worm (*Caenorhabditis elegans*), and crustaceans, have exhibited plasma membrane $Na^+/H^+$ exchangers (also called NHE) which exchange these ions at a ratio of 1:1. Prokaryotes have functionally similar $Na^+/H^+$ exchanger proteins which also regulate intracellular $Na^+$ ion concentration and pH, and exchange one intracellular $Na^+$ for one $H^+$.

In eukaryotic cells, the plasma membrane $Na^+/H^+$ exchangers have multiple functions, including pH homeostasis, volume regulation, cell proliferation, and transcellular $Na^+$ absorption. In no cell, however, is the $Na^+/H^+$ exchanger the only mechanism for these functions. For instance, pH homeostasis is controlled in most eukaryotic cells by mechanisms including a $Cl^-/HCO_3^-$ exchanger, a $NaHCO_3^-$ co-transporter, a $NA^+$-dependent $Cl^-/HCO_3^-$ exchanger, and multiple mechanisms of $H^+$ extrusion.

Nonetheless, understanding the $Na^+/H^+$ exchanger will greatly increase the understanding of the body's control of ions, and much work has been done on the $Na^+/H^+$ exchanger family. Four mammalian $Na^+/H^+$ exchanger isoforms have been cloned (NHE1–4) (28). Of these, NHE3 appears to be the $Na^+/H^+$ exchanger isoform that is most likely responsible for "brush border" $Na^+/H^+$ exchange activity.

The brush border consists of microvilli, approximately 1$\mu$ in length and 0.1$\mu$ in diameter, that protrude from the surface of epithelial cells on the intestine and renal tubules. These microvilli greatly increase the surface area of those cells. Brush border $Na^+/H^+$ exchange activity contributes to transepithelial neutral NaCl absorption (38) in the small intestine, and to $Na^+$ reuptake in the proximal renal tubule (11,12,16). Additionally, brush border $Na^+/H^+$ exchange activity is important in the secretion of acid in the proximal renal tubule (1).

Thus, a malfunctioning $Na^+/H^+$ exchanger affects a body's well being. In chronic metabolic acidosis, chronic renal failure, diabetic nephropathy, and in animal models of essential hypertension, one observes an increase in renal proximal tubule brush border $Na^+/H^+$ exchange activity (16,18). More specifically regarding hypertension, increased $Na^+/H^+$ exchange in the renal proximal tubule or cortical thick ascending limb of Henle would enhance $Na^+$ reabsorption, leading to a defect in renal $Na^+$ excretion (16). It has been shown that defective renal $Na^+$ excretion is a cause in some patients of essential hypertension (16).

Similarly, increased jejunal brush border $Na^+/H^+$ exchange has been shown to be present in animal models of essential hypertension (40). Increased ileal and renal brush border $Na^+/H^+$ exchange activity is an important mechanism for the increased ileal and renal NaCl and water absorption that occurs in response to administration of glucocorticoids (34,41) and thus may, in part, be responsible for common side-effects of glucocorticoid pharmacologic therapy in humans such as hypertension and fluid and salt retention.

Conversely, decreased brush border $Na^+/H^+$ exchange activity is the major mechanism for decreased $Na^+$ and water absorption in most human diarrheal diseases (21). In one familial diarrheal syndrome, congenital sodium diarrhea, there is evidence of a congenital absence of jejunal brush border $Na^+/H^+$ exchange activity (4).

NHE3 is believed to be the $Na^+/H^+$ exchanger that is increased in the above renal diseases and inhibited in diarrheal diseases because the $Na^+/H^+$ exchange activity of NHE3 is most like that of ileal villus cell brush border membranes: it is relatively resistant to $Na^+/H^+$ exchange inhibition by amiloride, and it is the only $Na^+/H^+$ exchanger isoform inhibited and not stimulated by protein kinase C (28). Furthermore, only NHE3 message expression increases in parallel with the increased ileal villus apical $Na^+/H^+$ exchange activity in rabbits treated for 24h with methylprednisolone (34). Recent immunohistochemical studies and Western analysis have demonstrated that NHE3 is present on the brush border but not the basolateral membranes of ileal villus and ascending colon surface epithelial cells and proximal renal tubules (2,3). Therefore, NHE3 is believed to be the $Na^+/H^+$ exchanger isoform responsible for the characteristic $Na^+/H^+$ exchange activity of the brush border membranes of the mammalian small intestinal, colonic and proximal renal tubule $Na^+$ absorbing cells (14,28).

In addition, activation of plasma membrane $Na^+/H^+$ exchange has been postulated to play an important role in oncogenic transformation, and inhibitors of plasma membrane $Na^+/H^+$ exchange activity have been shown to have antitumoral effects (16,42).

A partial human NHE3 cDNA, clone HKC-3, which encodes 325 amino acids having 94% identity to rabbit NHE3 residues 180–505, has been previously reported (26). Clone HKC-3 has been used to physically and genetically map human NHE3 to chromosome 5p15.3, making NHE3 the most telomeric gene identified on chromosome 5p (6) and proving that the human NHE3 homologue arises from a different gene than human NHE1, mapped to 1p (15). Nonetheless, the existence of the clone did not provide the full DNA sequence of human NHE3 or the protein itself, and there remained in the art a need for that sequence.

SUMMARY OF THE INVENTION

The present invention provides the full cDNA sequence of human NHE3 as well as the deduced amino acid sequence of NHE3. The invention also provides an expression vector comprising the DNA encoding human NHE3, as well as a host cell transformed with the vector. Such a transformed host cell can be used as a screen for drugs that affect the $Na^+/H^+$ exchanger.

BRIEF DESCRIPTION OF THE FIGURES

FIGS. 3A–3B. These figures set forth the nucleotide sequence of the human NHE3 composite cDNA (above) (SEQ ID NOS: 7 and 8) and the deduced amino acid sequence of the protein (below) (SEQ ID NO:9).

FIGS. 4A–4B. These figures demonstrate the alignment of the amino acid sequence of human NHE3 (HUMNHE3), (SEQ ID NO:10), rat NHE3 (RATNHE3) (SEQ ID NO:11), and rabbit NHE3 (RABNHE3) (SEQ ID NO:12).

DETAILED DESCRIPTION OF THE INVENTION

To obtain the full length human NHE3 gene, we prepared a composite cDNA made up of the DNA of three pieces:

clone HKC-3;

clone HKC-5, another NHE3 clone obtained using HKC-3 as a probe, which overlaps with HKC-3 and contains the entire 3' region of human NHE3; and clone 23-3, obtained using a new method described below. That composite cDNA is set forth in schematically in FIG. 1 while FIGS. 3A–3B provides the nucleotide sequence of the human NHE3 composite cDNA (above) and the deduced amino acid sequence (below).

We had previously reported a human NHE3 partial cDNA clone HKC-3 (26) (report providing only the putative amino acid sequence of HKC-3). Colony hybridization screening of the library that yielded HKC-3, as well as two other libraries, did not provide the complete 5' coding nucleotides of the NHE3 full length cDNA. Interestingly, the most 5' nucleotide sequence found was at a location homologous to the most 5' nucleotides of exon 2 of human NHE1, and it is known that a 41.5Kb intron separates exons 1 and 2 in human NHE1. Subsequent work in our laboratory supports the presence of a large intron segment between exons 1 and 2 that would make obtaining the 5' end difficult. We subsequently also determined that a segment in the 5' region is GC rich, further compounding the difficulty of cloning the 5' end.

Figures 2, 6:
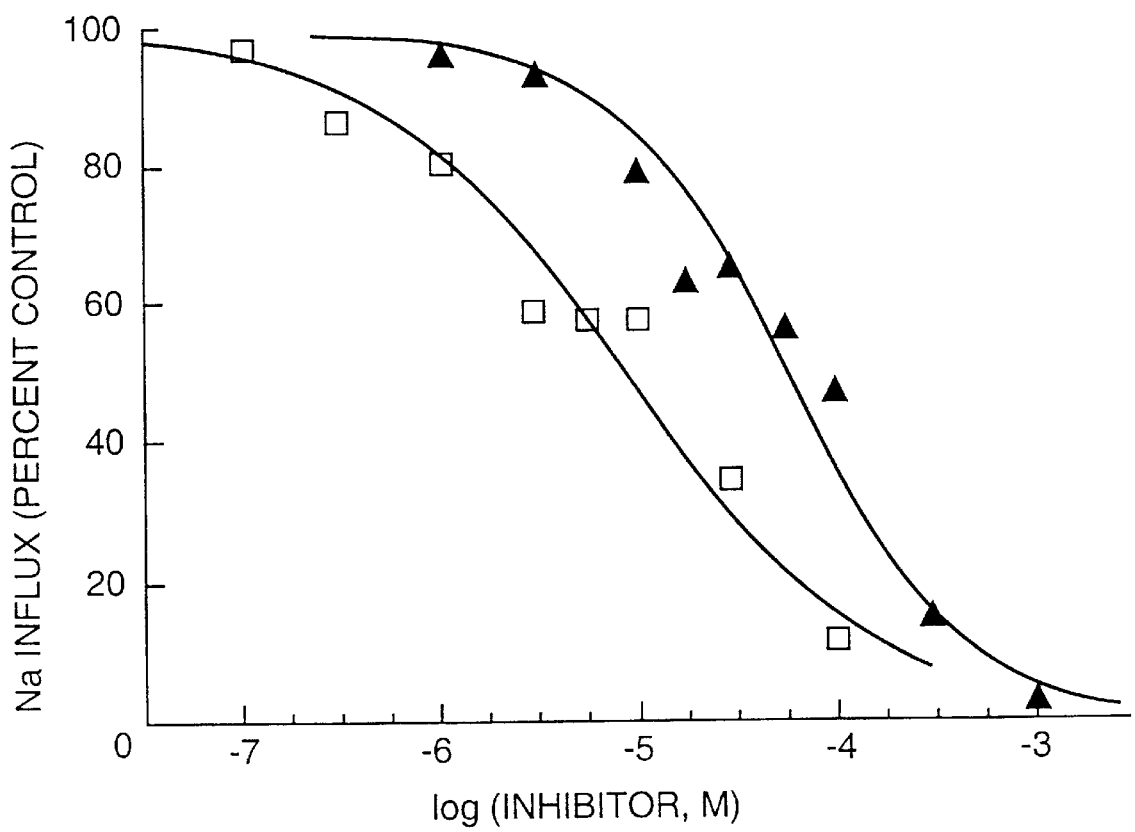
FIG. 2. This figure demonstrates the alignment of the minicistron sequences located in the 5' noncoding regions of rabbit NHE3 (SEQ ID NO:5) and rat NHE3 (SEQ ID NO:6) (20,26).
FIG. 6. This figure sets forth the concentration dependence curves for inhibition of $^{22}Na^+$ (1 mM) uptake in HNHE3/PS-120 cells by amiloride (Δ) and ethylisopropylamiloride (EIPA) (□).

Accordingly, we developed a new method to clone the 5' region. We first prepared a degenerate forward primer B8, developed from the sequences encoding minicistrons found in the 5' untranslated regions of both rabbit and rat NHE3 (FIG. 2). We ultimately obtained the remaining 5' coding region (clone 23-3) by reverse transcription/polymerase chain reaction (RT-PCR) of human kidney RNA, based on a reverse primer, B3, derived from HKC-3, and the forward primer B8.

The three pieces provided a composite of human NHE3 cDNA. Thus, an embodiment of the claimed invention is a DNA molecule encoding human NHE3 comprising the nucleotide sequence of FIGS. 3A–3B. Another embodiment of the invention is a DNA molecule, or fragment thereof, encoding human NHE3 comprising the 5' region of the nucleotide sequence of FIGS. 3A–3B.

The invention also includes an expression vector comprising the DNA molecule, or fragment thereof, encoding human NHE3 of FIGS. 3A–3B. A preferable expression vector is pECE. Another aspect of the invention is a host cell transfected with the expression vector containing the claimed DNA. One such host cell is PS120, a fibroblast cell derived from the Chinese hamster lung fibroblast cell line CCL39 that lacks all endogenous $Na^+/H^+$ exchangers.

In another embodiment, the claimed invention includes the protein or polypeptide encoded by the nucleotide sequence of FIGS. 3A–3B, or any fragment thereof.

In an important embodiment, the NHE3 of the invention is the characteristic $Na^+/H^+$ exchanger of the brush border of the kidney and small intestine. Thus, another embodiment of the invention relates to the use of a cell line transformed with NHE3 cDNA as a screen for drugs that affect the brush border of the kidney or small intestine. In a preferred embodiment, the transformant is PS120/NHE3.

Another unexpected finding of the invention is the tissue distribution of the claimed human NHE3. Unlike the limited presence of rat and rabbit NHE3 in kidney, stomach, some intestinal tissues, and brain, the claimed human NHE3 has been detected in a variety of epithelial and nonepithelial human tissues, ranging as follows: kidney>>small intestine>>testes>ovary>colon=prostate>thymus>peripheral leukocyte=brain>spleen>placenta, and including endothelial cells. No NHE3 was detected in the heart, lung, liver, skeletal muscle, or pancreas. Thus, in another embodiment, the invention relates to the use of a cell line transformed with NHE3 cDNA as a screen for drugs that affect cells other than the epithelium of the kidney or small intestine, such as the endothelium of man. In a preferred embodiment, the transformant is PS120/NHE3, especially in screening for drugs which are useful to treat or cure hypertension and other medical conditions, including but not limited to those as noted above.

The practice of the present invention will employ the conventional terms and techniques of molecular biology, microbiology, recombinant DNA, and biochemistry that are within the ordinary skill of those in the art. See, for example, Sambrook, et al., MOLECULAR CLONING: A LABORATORY MANUAL, 2nd ed. Cold Spring Harbor Laboratory Press (1985).

Nonetheless, we offer the following basic background information. DNA, deoxyribonucleic acid, consists of two complementary strands of nucleotides, which include the four different bases compounds, adenine (A), thymine (T), cytosine (C), and guanine (G). A of one strand bonds with T of the other strand while C of one strand bonds to G of the other to form complementary "base pairs", each pair having one base in each strand.

A sequential grouping of three nucleotides (a "codon") codes for one amino acid. Thus, for example, the three nucleotides CAG codes for the amino acid Glutamine. The 20 naturally occurring amino acids, and their one letter codes, are as follows:

| | | |
|---|---|---|
| Alanine | Ala | A |
| Arginine | Arg | R |
| Asparagine | Asn | N |
| Aspartic Acid | Asp | D |
| Asparagine or Aspartic acid | Asx | B |
| Cysteine | Cys | C |
| Glutamine | Gln | Q |
| Glutamine Acid | Glu | E |
| Glutamine or glutamic acid | Glx | Z |
| Glycine | Gly | G |
| Histidine | His | H |
| Isoleucine | Ile | I |
| Leucine | Leu | L |

-continued

| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Amino acids comprise proteins. DNA is related to protein as follows:

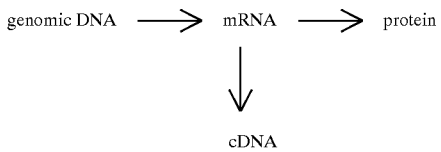

Genomic DNA is all the DNA sequences found in an organism's cell. It is "transcribed" into messenger RNA ("mRNA"). Complementary DNA ("cDNA") is a complementary copy of mRNA made in the laboratory by reverse transcription of mRNA. Unlike genomic DNA, both mRNA and cDNA contain only the protein-encoding regions of the DNA, the so-called "exons." Genomic DNA also includes "introns" which do not encode proteins.

Collections or "libraries" of genomic DNA and cDNA may be constructed in the laboratory or obtained from commercial sources. The DNA molecules present in the libraries may be of unknown function and chemical structure, and the proteins they encode may also be unknown. Nonetheless, one can attempt to retrieve specific desired DNA molecules from the libraries by screening the libraries with a gene probe. A gene probe bears a sequence that is complementary to the sequence of interest and will, accordingly, bond or "hybridize" with the sequence.

Once retrieved, the DNA can be sequenced using techniques that are standard in the art, such as Sanger's dideoxy termination procedure. To orient oneself on the DNA structure, it is referred to as having a 5' end and a 3' end based on the structure of the nucleotides that make up the DNA.

DNA can be cut, spliced, and otherwise manipulated using "restriction enzymes" that cut DNA at certain known sites and DNA polymerases that join DNA. Such techniques are well known to those in the art, as set forth in texts such as Sambrook, et al., MOLECULAR CLONING: A LABORATORY MANUAL, 2nd ed. Cold Spring Harbor Laboratory Press (1985).

DNA of a specific size and sequence can then be inserted into a "replicon", any genetic element, such as a plasmid, cosmid, or virus, that is capable of replication under its own control. A "recombinant vector" or "expression vector" is a replicon into which a DNA segment is inserted so as to allow for expression of the DNA, i.e., production of the protein encoded by the DNA. Expression vectors may be constructed in the laboratory, obtained from other laboratories, or purchased from commercial sources. Expression vectors that would be suitable for use in this invention include pECE and pMAMneo.

The recombinant vector (known by various terms in the art) may be introduced into a host by a process generically known as "transformation". Transformation means the transfer of an exogenous DNA segment by a number of methods, including infection, direct uptake, transduction, F-mating, microinjection, or electroporation into a host cell.

Host cells, known variously as recombinant host cells, cells, and cell culture, include microorganisms, insect cells, and mammalian cells. As those in the art recognize, the expression of the DNA segment by the host cell requires the regulatory sequences. The regulatory sequences vary according to the host cell employed, but include, for example, in prokaryotes, a promoter, ribosomal binding site, and/or a transcription termination site. In eukaryotes, such regulatory sequences include a promoter and/or a transcription termination site.

The DNA may be expressed as a polypeptide of any length such as peptides, oligopeptides, and proteins. Polypeptides also include translational modifications such as glycosylations, acetylations, phosphoralations, and the like.

Having provided this background information, we now describe preferred aspects of the invention.

We had previously described the cloning of a partial cDNA isolated from a human kidney cortex library, clone HKC-3, that had 94% amino acid identity to the previously characterized rabbit NHE3 $Na^+/H^+$ exchanger isoform (26). In the work underlying this invention, we have determined that HKC-3 represents a cDNA fragment of a functioning human NHE3 $Na^+/H^+$ exchanger isoform.

To extend the human cDNA beyond that of HKC3, we reprobed the human kidney cortex library using HKC3 as a probe. We identified an additional NHE3 clone, designated HKC5, which overlaps with clone HKC3 and contains the entire 3' coding and noncoding regions of human NHE3. Neither, however, provided the 5' coding region.

We ultimately obtained that region using reverse transcription/polymerase chain reaction (RT-PCR) of human kidney RNA, based on a reverse primer B3, derived from HKC3, and a forward primer, B8, a degenerate primer derived from the 5' region of both rabbit and rat NHE3 (FIG. 2). The RT-PCR amplification yielded clone 23-3 which contains the sought-after 5' coding sequence of human NHE3.

We created a composite human NHE3 based on these pieces.

Figure 1:
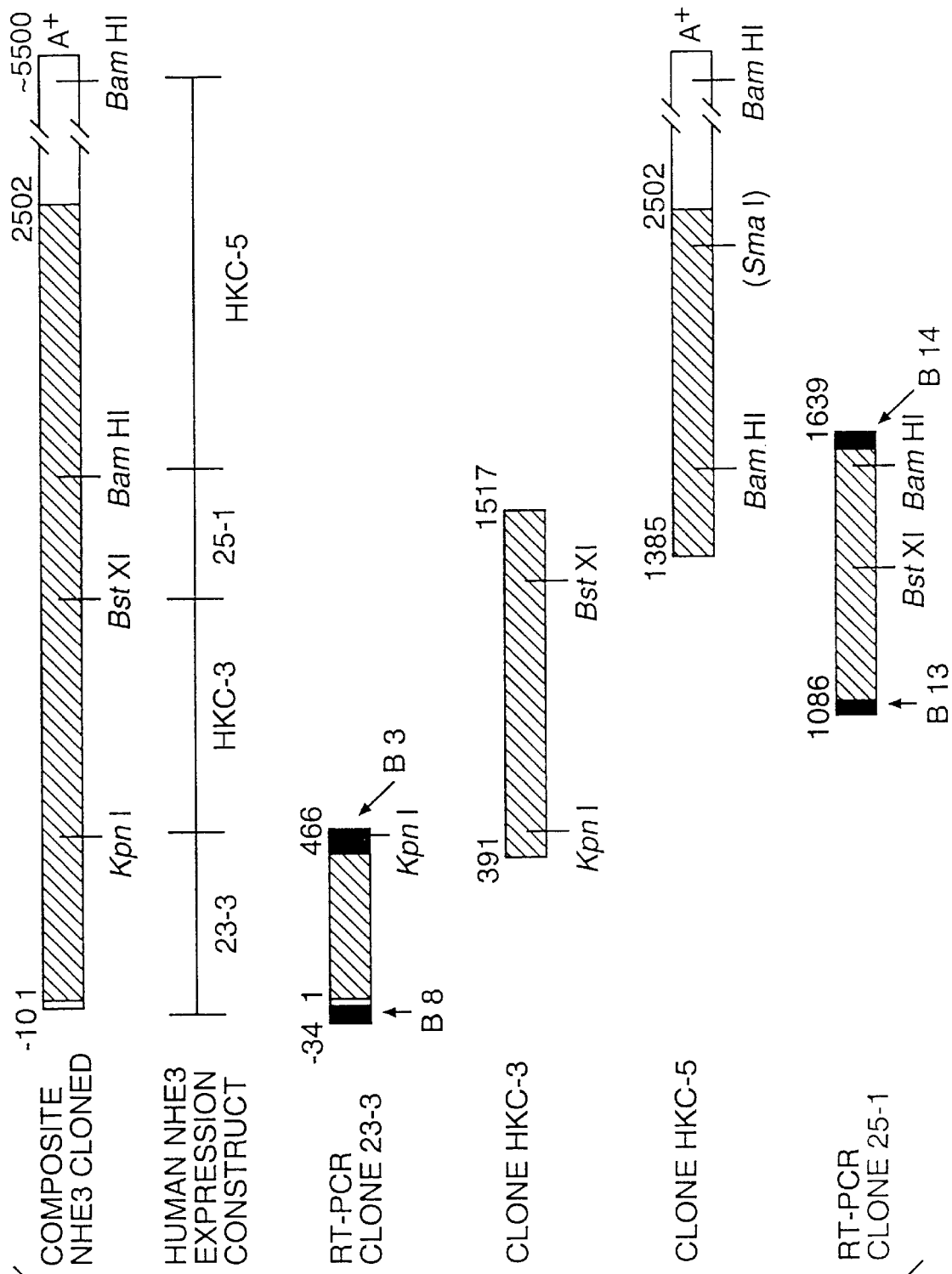
FIG. 1. This figure provides a schematic representation of human NHE3 composite cDNA and partial cDNA clones used in the cloning of human NHE3.

FIG. 1 provides a schematic representation of the human NHE3 composite while FIGS. 3A–3B provides the nucleotide sequence of the human NHE3 composite cDNA and deduced amino acid sequence.

The deduced amino acid sequence, based on the identity of the three-nucleotide codon, of human NHE3 is 834 residues and the calculated relative molecular weight is 92,906. FIGS. 4A–4B shows the alignment of the deduced amino acid sequences of the three cloned NHE3 homologues. Human NHE3 is 89% identical at the amino acid level to rat NHE3 and 88% identical to rabbit NHE3.

The human NHE3 composite cDNA was stably transfected into NHE deficient cell line, PS120, a NHE deficient derivative of the Chinese hamster lung fibroblast cell line CCL39 by $CaPO_4$ precipitation. Transfection allowed these cells to perform $Na^+/H^+$ exchange, assessed by $Na^+$ dependent alkalinization and measured by the fluorescence of the acetoxymethyl ester of 2',7'-bis(2-carboxyethyl)-5-(and-6) carboxyfluorescein (BCECF).

Human brush border epithelial $Na^+/H^+$ exchange has been characterized as being much less sensitive to inhibition by amiloride and its 5-amino-substituted analogues than basolateral and nonepithelial membrane $Na^+/H^+$ exchangers (10, 24,36). Thus, we assessed the sensitivity of human NHE3 to inhibition by amiloride and ethylisopropylamiloride (EIPA) by $^{22}Na^+$ uptake studies (FIG. 6). Our studies demonstrated that the sensitivity of human NHE3 is in the range of that of rabbit and rat NHE3 (Table 1) (19,29):

TABLE I

Effect of amiloride and ethylisopropylamiloride on human, rabbit and rat NHE3

| | Inhibition constants ($IC_{50}$ in $\mu M$) | |
|---|---|---|
| | Amiloride | Ethylisopropylamiloride |
| Human NHE3 | 49 | 6.6 |
| Rat NHE3 | 100 | 2.4 |
| Rabbit NHE3 | 39 | 8.0 |

In regards to amiloride and EIPA sensitivity, we note that the amino acid sequence of FFFYL in putative MSD 4, previously shown by Counillon et al. and Yun et al. to be a critical region in the determination of NHE amiloride and EIPA sensitivity (7,35), is entirely conserved among all three NHE3 homologues.

Figure 7A:
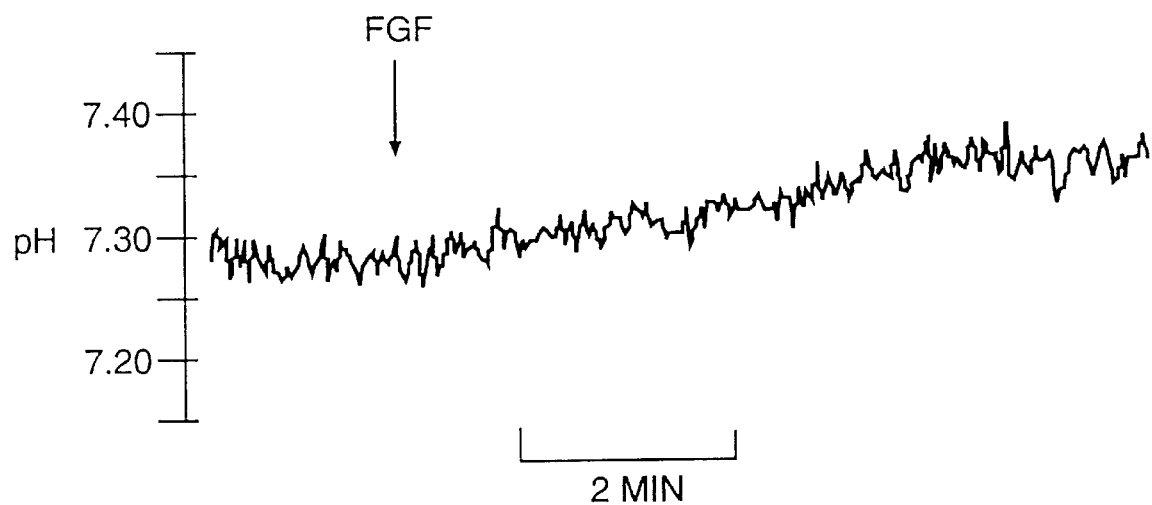
FIGS. 7A–7B. These figures provide tracings from representative experiments on the regulation of human NHE3 at steady state $pH_i$ by either 10 ng/ml FGF (A) or 1.0 μM PMA (B).
Figure 7B:
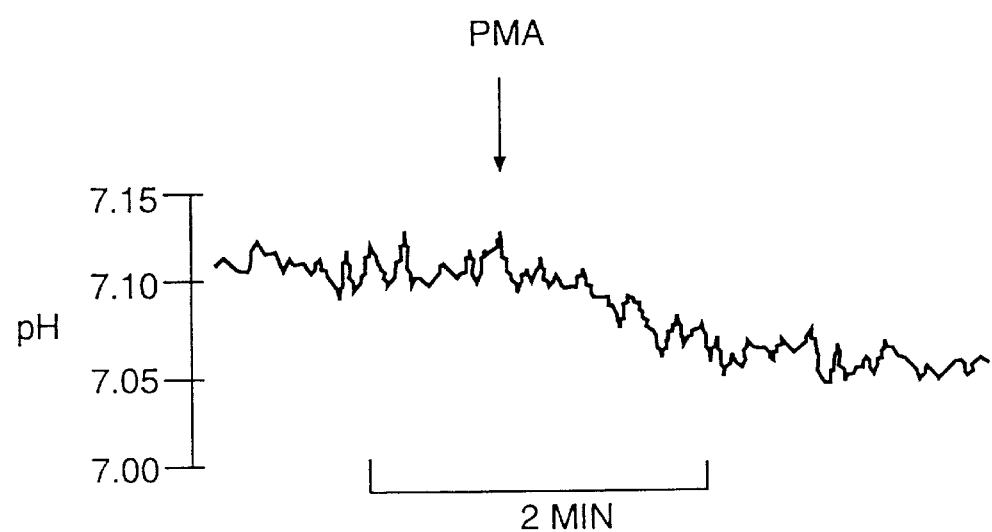

Also similar to rabbit and rat NHE3 (14,19,29), we found that human NHE3 was activated by FGF, an activator of a receptor tyrosine kinase, and was inhibited by PMA, an activator of protein kinase C (FIGS. 7A–7B). In the region C-terminal of MSD 10, which is essential for protein kinase regulation (5,32), there are 8 potential protein kinase C consensus sequences conserved among all three cloned $Na^+/H^+$ exchangers and a single conserved tyrosine kinase site at human NHE3 amino acid 546 (FIGS. 4A–4B). Nonetheless, there was no effect of 8-bromo-cAMP on human NHE3/PS120 cells, in spite of the presence of putative cAMP dependent protein kinase consensus sequences in the C-terminus. This was not surprising as none of the cloned mammalian $Na^+/H^+$ exchangers transfected into PS120 cells have been shown to be affected by addition of cAMP (28), although the cloned trout $Na^+/H^+$ exchanger (β-NHE) is regulated by cAMP in PS120 cells (5).

Across species, the overall sensitivity of NHE3 to amiloride inhibition and its regulation by second messengers is conserved. The relative amiloride resistance of human NHE3, its inhibition by PMA, and its expression being greatest in the kidney and small intestine is consistent with human NHE3 being the characteristic brush border $Na^+/H^+$ exchanger of these tissues. Indeed, recent Western analysis and immunohistochemical studies of human ileum and ascending colon, stained with antibody made against the rabbit NHE3 C-terminus, have confirmed that human NHE3 is present on the brush border membranes but not the basolateral membranes of human ileal villus and ascending colonic surface $Na^+$ absorbing epithelial cells (9). NHE3 is therefore a likely candidate to be the $Na^+/H^+$ exchanger isoform altered in diseases of the kidney and small intestine in which brush border $Na^+/H^+$ exchange activity is abnormal.

In this regard, we note that the literature reports that there is increased $Na^+/H^+$ exchange in the brush border of intestinal cells of patients with cystic fibrosis and that this likely contributes to the manifestations of the disease with desiccated luminal contents (37). A potential therapy for cystic fibrosis may be the inhibition of brush border $Na^+/H^+$ exchange. If such therapy is to succeed, drugs that inhibit brush border $Na^+/H^+$ exchange must be identified and tested. In one embodiment, a cell stably transfected with human NHE3 cDNA could be used to screen such drugs. In a preferred embodiment, the cell is PS120. Given the present disclosure, those of ordinary skill in this art could set up a screen to assess the affect of drugs on brush border $Na^+/H^+$ exchangers. For example, one could measure $Na^+/H^+$ exchanger activity by assessing $Na^+$ dependent alkalinization using fluorescence measurement with BCECF as set forth in the Methods section. Alternatively, one could measure $^{22}Na^+$ uptake, also as set forth in the Methods section.

Such screens may also be used for assessing drugs for the treatment of diarrhea. In virtually all diarrheal diseases, there is inhibition of brush border $Na^+/H^+$ exchange in the small bowel or colon (38). Accordingly, drugs that stimulate NHE3 may well be useful for the treatment of acute and chronic diarrhea, and the screens described above may be used to assess a drug's ability to stimulate NHE3. This methodology, in summary, could be used as a screen to assess the affect of drugs for conditions where either NHE3 may be malfunctioning and/or the modification of NHE3's native $Na^+/H^+$ exchange activity may have a potential therapeutic benefit.

Human NHE3, like rabbit NHE1, rabbit NHE2 and rabbit NHE3, exhibited evidence of a $H^+$ modifier site, with Hill coefficients of ≅2 (14). As we have noted previously, this contradicts some vesicle transport studies claiming that ileal brush border and basolateral, and colonic brush border membranes $Na^+/H^+$ exchangers have non-allosteric, Michaelis-Menten relationships between $[H^+]$ concentration and $Na^+/H^+$ exchange rate (27). The affinity of human NHE3 for $H^+$ (K') was likewise similar to that reported for rabbit NHE2 and NHE3 (14).

Unlike NHE3 in the rat and rabbit, we found that human NHE3 message is expressed in a variety of both epithelial and nonepithelial tissues. NHE3 in the rat and rabbit has not been detected in any tissues outside the kidney and the gastrointestinal tract, with the exception of one recent study by Bookstein, et al. reporting faint message detection in the rat brain (3,20,26). NHE3 expression has not been examined in the rat or rabbit ovary, prostate, thymus, leukocyte, or placenta (20,26). Orlowski et al. detected no NHE3 message in the rat testes or spleen, in contrast to our finding of relatively abundant NHE3 message in the human testes, and relatively low message in the human spleen. In the human, therefore, NHE3 most likely has significant roles in other tissues, for which the transepithelial absorption of $Na^+$ is not thought of as a primary physiologic function.

The relative degree of expression of human NHE3 in kidney and gut tissues is similar to that found for the rabbit (26), although human NHE3 expression in the colon was much less than in the small intestine whereas rabbit NHE3 expression in the ascending colon was equal to that found in the ileum. Some of these differences may be attributed to sampling differences, as the human colon mRNA studied was derived from both the ascending and transverse colon. Interestingly, message expression of human NHE3 for the kidney and gut is opposite that found in the rat, in which two studies report message expression in the following order: colon>small intestine>kidney (3,20). It is noteworthy that in the human, NHE3 message of two sizes (6.7 and 8.9 kb) is expressed nearly equivalently in all tissues except the kidney and gut. In these latter two organs, expression was almost completely limited to the 6.7 kb band.

We provide the following specific methods that may be used in the practice of the claimed invention. It is to be understood that both the foregoing general description and the following detailed description are exemplary and explanatory only and are not restrictive of the invention as claimed.

METHODS

In conducting the experiments described in the Examples below, we used the following methods:

cDNA Library Screening.

The human NHE3 partial cDNA clone, HKC3, was used to rescreen, under conditions of high stringency (hybridized at 42° C. in 50% formamide, 4×SSC, 5×Denhardt, 1% sodium dodecyl sulfate (SDS) and washed at 62° C. in 0.15×SSC and 0.1% SDS) the same human kidney cortex λgt10 cDNA library from which it was isolated (obtained from Dr. G. I. Bell, the University of Chicago). Six positive clones were identified, and their cDNA inserts were subcloned into plasmid pBluescript II KS (Stratagene) and sequenced on both ends. One of these clones, HKC5, was further characterized (FIG. 1).

RT-PCR cloning.

To obtain 5' human NHE3 sequence, 1 μg of human kidney RNA, obtained from Dr. Pat Wilson (The Johns Hopkins Univ.), was reverse transcribed (RT), using random primers into cDNA using the SuperScript Preamplification System for First Strand cDNA Synthesis kit (GIBCO) according to the manufacturer's recommendations. 2 μl of RT product was used as template in a 50 μl polymerase chain reaction (PCR) (39) containing (final amounts/concentrations) 10×PCR II buffer (5 μl), deoxynucleotides (300 μM), formamide (3%), Taq polymerase (Perkin Elmer Cetus) (2 U), reverse HKC3 primer B3 (5'-GCGAATTCCACACGGTACCCACGAC-3') (30 pmol) SEQ ID NO:1 and degenerate NHE3 minicistron forward primer B8 5'-ATGCG (G/A/T/C)GT CGG(G/A/T/C) (C/T) CC (C/T)GG (C/A)GC TGAGC-3' (30 pmol) SEQ ID NO:2. B8 was based on the conserved minicistrons of rabbit and rat NHE3 (FIG. 2) (20,26).

Amplification was performed for 30 cycles: 94° C. (75 s), 59° C. (45 s), and 72° C. (2 min). PCR product was separated on a 1.4% agarose gel and blotted onto nylon filters (Hybond). Filters were probed under high stringency conditions with a rabbit 5' NHE3 partial cDNA, clone RAI1 (26), to analyze for homologous 5' human NHE3 PCR product. Hybridizing RT-PCR clone 23-3 was subcloned into plasmid pCR II using the TA Cloning Kit (Invitrogen) and sequenced (FIG. 1).

cDNA Sequencing.

Sequencing of the coding region of human NHE3 cDNA clones was performed on both strands by Sanger's dideoxy termination procedure using the Sequenase kit (USB Corp) (22). ExoIII/mung bean nuclease digestion was used to obtain progressive unidirectional deletion clones (26). Two regions of high GC content containing compression artifact (RT-PCR clone 23-3 and between nucleotides 2333 to 2571) were also sequenced using internal primers and the fluorescent dideoxy terminator method of cycle sequencing on an Applied Biosystems (Foster City, Calif.) 373a automated DNA sequencer, following ABI protocols at the DNA Analysis Facility of Johns Hopkins University (17,25).

Construction of a full length human NHE3 Na+/H+ exchanger composite cDNA.

Three overlapping clones, RT-PCR clone 23-3 and the human kidney cortex cDNA clones HKC3 and HKC5, produced the entire coding sequence of human NHE3 (FIG. 1). A 554 bp overlapping human NHE3 fragment (RT-PCR clone 25-1) was amplified to facilitate joining HKC3 and HKC5, and thereby enable construction of a human NHE3 expression construct: human kidney RNA was reverse transcribed as above and PCR amplification, using standard techniques, was performed using human NHE3 specific primers, forward primer B13 (5'-CATCTGGACCTGGAACACG-3') SEQ ID NO:3 and reverse primer B14 (5–CGTAGCTGATGGCATCCTTC-3') SEQ ID NO:4. The identity of RT-PCR clone 25-1 was confirmed by sequencing. To create a composite NHE3 full-length coding cDNA, clones 25-1, HKC5, HKC-3 and 23-3 were subcloned into a pUC 19 vector using the restriction sites as noted in FIG. 1 and standard restriction digestion and ligation techniques. The NHE3 composite cDNA construct contained 10 bp of 5' untranslated NHE3 cDNA, the entire coding region of human NHE-3 and 2.2 kb of 3' untranslated cDNA sequence (FIG. 1, human NHE3 expression construct). This was subcloned directionally into the EcoRI/XbaI sites of the eukaryotic expression vector pECE (35) to create human NHE3 expression plasmid, pEH3.

Stable expression of the human NHE3 composite cDNA in Na+/H+ exchange deficient fibroblasts.

The pEH3 construct was stably cotransfected with pSV2neo (Clontech) into the Na+/H+ exchanger deficient cell line PS120, a Na+/H+ exchanger deficient derivative of the Chinese hamster lung fibroblast cell line CCL39, by the method of CaPO$_4$ precipitation as described previously (23). Transfected cells (HNHE3/PS120 cells) were selected by both G418 resistance and the acid loading technique (23,30).

Measurement of Na+/H+ exchange activity: Fluorescence measurement with BCECF.

HNHE3/PS120 cells were grown to 70–80% confluency on glass coverslips, serum starved overnight to arrest growth, washed with Na+ medium (containing in mM: 130 NaCl, 5 KCl, 2 CaCl$_2$, 1 MgSO$_4$, 1 NaPO$_4$, 25 glucose, 20 HEPES, pH 7.4) and loaded with the acetoxymethyl ester of 2',7'-bis(2-carboxyethyl)5-(and-6)carboxyfluorescein (BCECF) as previously discussed (31). Cells were washed with TMA medium (containing in mM: 130 tetramethylammonium-Cl, 5 KCl, 2 CaCl$_2$ 1 MgSO$_4$, 1 TMA-PO$_4$, 25 glucose, 20 HEPES, pH 7.4), mounted in a cuvette, and perfused at 37° C. Cells were acidified by perfusing with 30 mM NH$_4$Cl prepulse followed by removal of NH$_4$Cl with TMA medium. The cuvette was then perfused with Na+ medium. Na+ dependent alkalinization, which was amiloride sensitive, as determined by BCECF fluorescence, was measured in an SLM spectrofluorometer as described (31). Na+/H+ exchange was determined by multiplying the initial rate of Na+ dependent alkalinization by intracellular buffering capacity, as described.

To determine the Hill coefficient n and the apparent H+ affinity constant K', a kinetic measure of H+ exchange (1), we obtained a plot of intracellular [H+] concentration versus rate of proton efflux by calculating the first-order derivative of the Na+-dependent pH recovery curve X intracellular buffering capacity, as previously described (14). Data points generated from 8 coverslips were recorded at 3 s intervals during the rapid phase of pH recovery, with longer (15 s) intervals between data points as the rate of alkalinization slowed. Data were analyzed using a nonlinear regression data analysis program (ENZFITTER, Biosoft Corp.).

$^{22}$Na+ uptake studies.

Stably transfected HNHE3/PS 120 cells were grown to near confluency in 24-well plates. The cells were serum-starved for 24 hours to arrest growth. $^{22}$Na+ uptake (1 mM) was measured during the linear phase of uptake in the presence of 1 mM ouabain and various concentrations of potential inhibitors amiloride or ethylisopropylamiloride (EIPA) following acidification with NH$_4$Cl prepulse, as detailed previously (30).

Northern blot analysis and RT-PCR confirmation of results.

Commercially available human Northern blots, human MTN and human MTN II (Clontech), each containing poly(A)+ RNA, 1 μg per lane, from 8 different human tissue types, were probed with the 953 bp 5' SmaI fragment of clone HKC5 (see FIG. 1) encoding amino acids 462 through 775, according to the manufacturer's instructions for high stringency probing. $2 \times 10^6$ cpm of randomly primed, $^{32}$P-labelled probe was added to each ml of hybridization solution. Blots were analyzed by autoradiography using Kodak XAR film.

EXAMPLE 1

Cloning and sequencing of a composite cDNA encoding human NHE3

To extend the human NHE3 cDNA beyond that of the previously reported human NHE3 partial cDNA clone, HKC3, we reprobed the human kidney cortex library using HKC3 as a probe and identified an additional NHE3 clone, HKC5 (FIG. 1). Clone HKC5 overlapped with clone HKC3 and contained the entire 3' coding and noncoding region of human NHE3, including the poly(A)$^+$ tail. It has been surprisingly found that, despite extensive efforts to utilize colony hybridization library screening of the same lamda gt10 human kidney from which HKC3 was isolated, we were unable to isolate the complete 5' coding nucleotides of the NHE3 full length cDNA.

The most 5' clone isolated was HKC-10, which encoded human NHE3 cDNA 182 nucleotides 5' of clone HKC3, at putative membrane spanning domain 2 as based on homology with the rabbit NHE3. Interestingly, the most 5' nucleotide sequence of clone HKC-10 was at a location homologous to the most 5' nucleotides of exon 2 of human NHE1. It is known that a 41.5 Kb intron separates exons 1 and 2 in human NHE1 (44). We have very recently obtained a human NHE3 genomic DNA cosmid clone, clone 84C11, and have found that, as in NHE1, an intron/exon boundary is likewise present in NHE3 immediately 5' to clone HKC-10. Furthermore, this cosmid clone does not contain human NHE3 putative exon 1, suggesting that the human NHE3 exon 1 is most likely separated from exon 2 by a relatively large intron, as found in NHE1. It may be that a large intron segment between exons 1 and 2 may have made obtaining NHE3 cDNA clones encoding exon 1 difficult.

Additionally, as we later determined, there ultimately was found to be a segment in the 5' coding region of NHE3, between coding nucleotides 12 to 107 (FIGS. 3A–3B) which was 87% GC rich. As noted below, this high GC rich region also was found to make the molecular cloning and sequencing of the 5' region of NHE3 difficult, and required a modification of the usual methodology.

We also screened three cDNA libraries, this same human kidney cortex lamda gt10 library and both human jejunal lamda gt11 and a human fetal kidney lamda gt10 libraries, by a polymerase chain reaction method of library screening using a modification of the method described by Tung et al. and using NHE3 specific antisense primers derived from HKC3 and HKC-10 sequence (43). Additional 5' human NHE3 clones were identified from these other libraries but no clones contained the entire remaining 5' coding nucleotides of NHE3. Therefore, after screening three libraries that had NHE3 5' clones but not the entire 5' coding segment, we embarked on a new method to clone this region.

A degenerate forward primer B8, was developed from the sequences encoding minicistrons found in the 5' untranslated regions of both rabbit and rat NHE3 (FIG. 2; Nucleotide identity is designated by "*"). (20,26). We ultimately obtained the remaining 5' coding region, by reverse transcription/polymerase chain reaction (RT-PCR) of human kidney RNA, based on a reverse primer B3, derived from HKC3, and the forward primer B8. The RT-PCR amplification yielded a 500 bp PCR product, clone 23-3, that had high homology with the 5' coding region of rabbit NHE3. Its sequence contained the remaining 5' coding sequences of human NHE3 and ten 5' noncoding nucleotides, between the minicistron primer sequence and the putative ATG start site.

Due to the high GC rich segment in this region as noted above (the region from bp 12 to 107 has 87% GC content), the polymerase chain reaction amplification of this region required using 3% formamide as a denaturant. Similarly, this region could not be sequenced correctly using Sanger's dideoxy termination procedure (22). Rather, it required amplifying the region using the polymerase chain reaction with addition of 200 μM 7-dcaza-dGTP (to weaken the GC hydrogen bonds that interfere with polymerization fidelity) and 100 μM dGTP in place of 300 μM dGTP nucleotide alone, then electroeluting the amplified PCR product. The electroeluted PCR product was directly sequencing by using internal primers and the fluorescent dideoxy terminator method of cycle sequencing on an Applied Biosystems (Foster City, Calif.) 373a automated DNA sequencer, following ABI protocols at the DNA Analysis facility of Johns Hopkins University (17, 25).

FIG. 1 shows a schematic diagram of the human NHE3 composite cDNA. The open reading frame is represented by the hatched area and the noncoding regions by the open bars. Nucleotide numbers are indicated on the top of the clones. Primers (B3, B8, B13, and B14) used to amplify NHE3 RT-PCR clones are represented by shaded bars. Each primer's name is listed below and separated by an arrow from its corresponding bar. Restriction enzyme sites used in constructing a composite human NHE3 cDNA or used in constructing a human NHE3 cDNA probe (i.e. SmaI) are indicated by the vertical lines intersecting the clones. The human NHE3 cDNA construct used in the expression studies is represented by the solid horizontal bar ("Human NHE3 Expression Construct"). The partial cDNA clones used to produce this construct are designated underneath this bar. They are separated by vertical lines representing the points of their restriction digestion and ligation.

The nucleotide and amino acid sequences of human NHE3 are presented in FIGS. 3A–3B. Nucleotides are numbered at the right of the sequence with respect to their putative translation initiation site. Amino acids are numbered at the left of the sequence and are represented by their single letter abbreviations. "*" represents an in-frame stop codon.

This nucleotide sequence shares 82% identity with rat NHE3 and 81% identity with rabbit NHE3 (20,26). The largest open reading frame, a series of codons coding for amino acids which is translatable into a protein, is 2502 bp, 9 bp larger than that of rat NHE3 and 6 bp larger than that of rabbit NHE3. The initiation codon is in fair agreement with Kozak's consensus sequence, having a G at bp −3 but a T at bp +4 (13). The next in-frame initiation codon is at MSD 4. Based on the size of clone HKC5, the 3' untranslated region of NHE3 is roughly 3 kb, of which the most 5-prime 72 bp and the 3' polyadenylation sequence have been determined. There was 74% identity between the first 39 bp 3' untranslated nucleotides of human and rat NHE3. Homology 3' of this region between human and rat NHE3 is insignificant. Only the first 38 bp 3' noncoding nucleotides of rabbit NHE3 have been identified (26); these have 92% identity with human NHE3.

The deduced amino acid sequence, based on the identity of the three-nucleotide codon, of human NHE3 is 834 residues. The calculated relative molecular weight is 92,906.

FIGS. 4A–4B shows the alignment of the deduced amino acid sequence of the three cloned NHE3 homologues. Rat NHE3 sequence was obtained from Orlowski et al. and rabbit NHE3 from Tse et al. (20,26). Amino acids are indicated by their single letter abbreviation. Membrane spanning domains are overlined (m1–m10, m5a, and m5b)

and were used as previously determined for rabbit NHE3 (26). Eight conserved putative protein kinase C phosphorylation consensus sequences are indicated by "#" overlying the serine or threonine residue. A single conserved tyrosine kinase phosphorylation consensus sequence is indicated by "+". Identical amino acids are indicated by "*", and "." indicates similarity. Amino acid numbers are shown on the right.

The three cloned NHE3 homologues are overall 82% identical; human NHE3 is 89% identical at the amino acid level to rat NHE3 and 88% identical to rabbit NHE3. As found for the NHE1 homologues (20,23,31), amino acid homology across species for NHE3 is greatest in the region between MSD 2–10; human NHE3 and rat NHE3 are 94% identical in this region as is human NHE3 and rabbit NHE3. The NHE3 proteins, again like the NHE1 proteins, diverge most near their N-termini; human and rabbit NHE3 identity is 62% N-terminal of MSD 2, and human and rat NHE3 identity is 49%. The cytoplasmic tails of the NHE3 proteins are highly conserved, 88% identity for human and rabbit NHE3 and 89% identity for human and rat NHE3. A single N-linked glycosylation consensus sequence is present at human NHE3 amino acid 326, and is conserved among all mammalian $Na^+/H^+$ exchanger isoforms (28).

EXAMPLE 2

Functional characterization of human NHE3 cDNA in $Na^+/H^+$ exchanger deficient fibroblasts To characterize the kinetic properties of human NHE3, we created a composite human NHE3 cDNA from the four human NHE3 partial cDNA clones diagrammed in FIG. 1. This composite cDNA contained the minicistron primer B8 sequence at its 5' most end, the 10 intervening 5' untranslated nucleotides, the entire coding sequence and 2.2 kb of the 2.9 kb 3' untranslated sequence. This cDNA was subcloned into the expression vector pECE, then stably transfected into the $Na^+/H^+$ exchanger deficient cell line PS120. The stably transfected human NHE3/PS120 cells (HNHE3/PS120), following acidification, showed rapid alkalinization upon addition of 130 mM $Na^+$ (FIG. 5A).

Figure 5A:
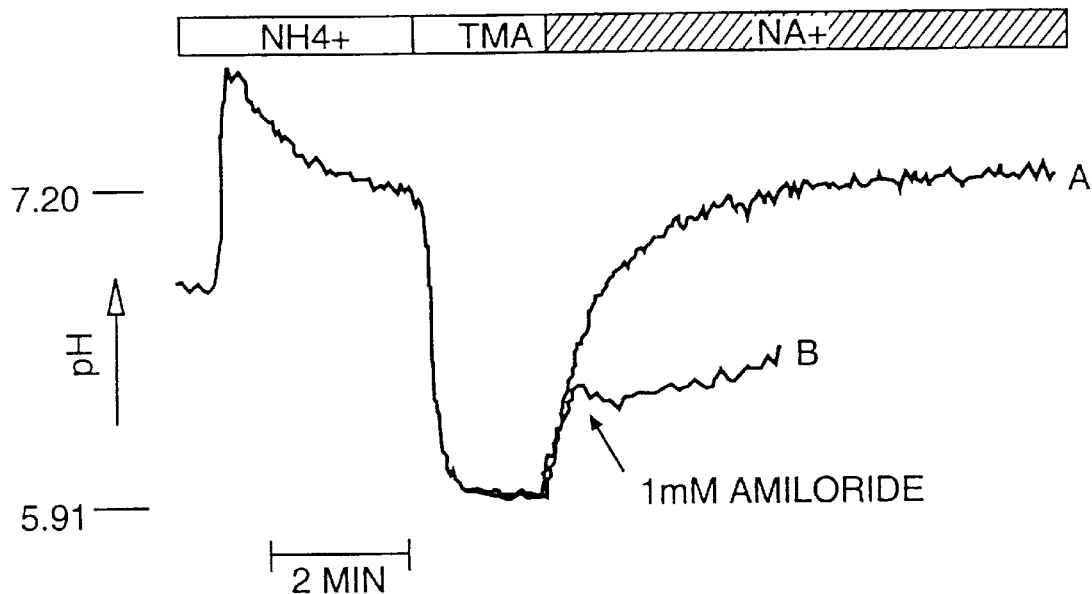
FIGS. 5A–5B. These figures provide a functional characterization of cells stably transfected with human NHE3 cDNA. A sets forth a composite tracing of two representative experiments on $pH_i$ recovery and B demonstrates $H^+$ efflux rate as a function of intracellular $[H^+]$ concentration.

FIG. 5A sets forth a composite tracing of two representative experiments demonstrating $pH_i$ recovery of PS120 cells stably transfected with the human NHE3 expression vector pEH3. HNHE3/PS120 cells loaded with BCECF were acidified by $NH_4Cl$ prepulse. In the presence of 130 mM $Na^+$ medium (curve A), but not 130 mM TIA medium, cells were able to recover to a steady-state $pH_i$. Addition of 1 mM amiloride in the presence of 130 mM $Na^+$ medium inhibits this recovery (curve B), proving that cloned human NHE3 is an amiloride inhibitable $Na^+/H^+$ exchanger.

Figure 5B:
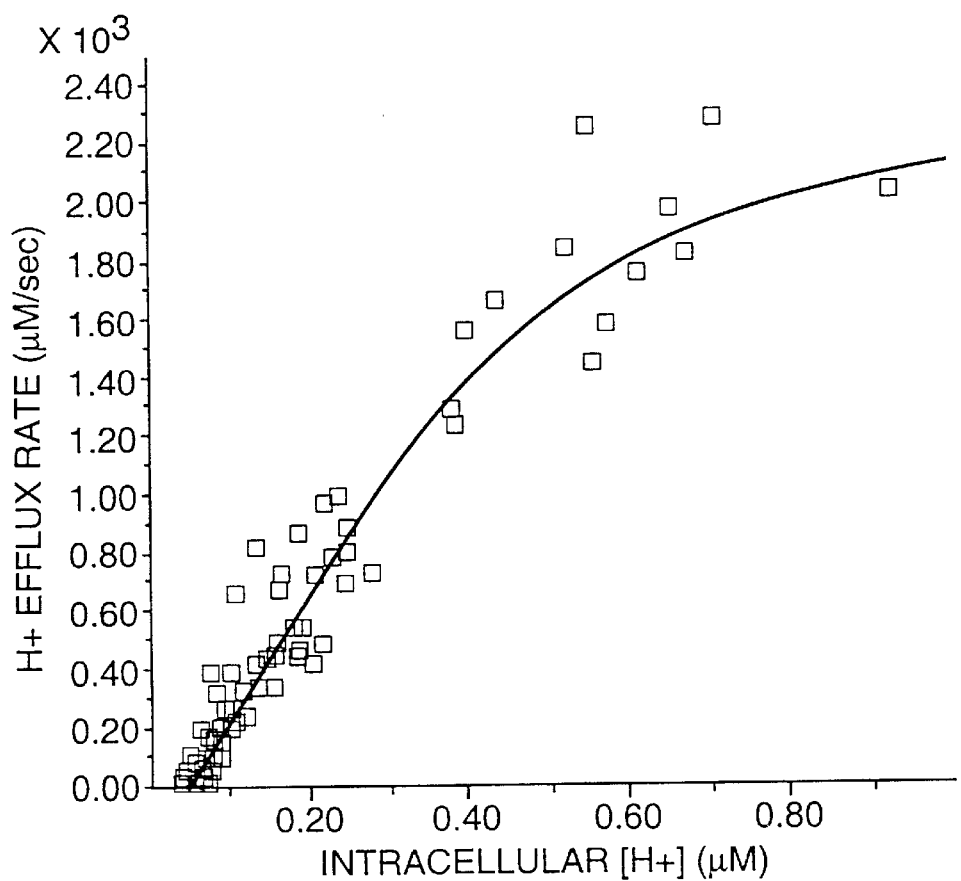

FIG. 5B demonstrates that the $Na^+/H^+$ exchange activity of HNHE3/PS120 cells with respect to intracellular $[H^+]$ concentration fits a sigmoidal rather than hyperbolic curve, demonstrating cooperative allosteric kinetics: Hill coefficient ($n_{app}$) was 2.0 and the apparent $H^+$ affinity constant K' was 0.164 $\mu M$. Specifically, we conducted a kinetic analysis of HNHE3/PS120 cells, expressed as $H^+$ efflux rate, as a function of intracellular $[H^+]$ concentration. HNHE3/PS120 cells were plated on eight glass coverslips and serum starved overnight. Initial rates of $pH_i$ recovery were obtained by calculating the first-order derivative of eight $pH_i$ recovery traces, a single trace as shown in FIG. 5A. $Na^+/H^+$ exchange rates ($\mu M$ $H^+$ per s)(□) were determined as described in Methods. The line in the plot was generated by the computer program using the Hill equation and was the best fit with the data. As noted above, the Hill coefficient ($n_{app}$) was 2.0; the apparent $H^+$ affinity constant K' was 0.164 $\mu M$ and $V_{max}$ was 2400 $\mu M$/sec.

Human brush border epithelial $Na^+/H^+$ exchange has been characterized as being much less sensitive to inhibition by amiloride and its 5-amino-substituted analogues than basolateral and nonepithelial membrane $Na^+/H^+$ exchangers (10, 24,36). Therefore we determined the quantitative sensitivity of HNHE3/PS120 cells to inhibition by amiloride and EIPA by $^{22}Na^+$ uptake studies. The concentration dependence for amiloride and EIPA inhibition of the initial rate of $^{22}Na^+$ uptake (1 mM) into acid loaded HNHE3/PS120 cells was determined.

Three independent experiments were performed. The mean $IC_{50}$ values for amiloride and EIPA were 49.0 $\mu M$ and 6.6 $\mu M$, respectively. FIG. 6 provides curves are from a representative experiment. Each point represents the mean percent of control $^{22}Na^+$ uptake of duplicate experiments for each concentration of inhibitor. The curves are nonlinear least squares fits of the data assuming a single binding site for the inhibition (GraphPAD Software, Inc., San Diego, Calif.). The $IC_{50}$ values for these representative curves were calculated to be 59 and 8.8 $\mu M$ for amiloride and EIPA, respectively.

To determine second messenger regulation of human NHE3, we studied the effects of fibroblast growth factor (FGF), the cAMP analogue 8-bromo-cAMP, and phorbol 12-myristate 13-acetate (PMA). Serum starved HNHE3/PS120 cells were acidified by a $NH_4Cl$ prepulse and allowed to recover in 130 mM $Na^+$ medium until steady-state $pH_i$ was obtained. Either FGF (10 ng/ml), 8-bromo-cAMP (0.5 mM) or PMA (1.0 $\mu M$) was then added at the times indicated in FIGS. 7A–7B. In comparison to controls, addition of FGF caused activation of the HNHE3/PS120 cells, which reached a new steady state after an average of 5 min (FIG. 7A); $\Delta pH_i$ was +0.051±0.016 following addition of FGF versus −0.006±0.012 for controls followed over a similar time period (p<0.035, n=4). Addition of 8-bromo-cAMP at steady state had no measurable effect on $Na^+/H^+$ exchange activity (n=2). PMA, in contrast, resulted in a fall of the $pH_i$ from its steady-state value, reaching a new steady state after an average of less than 2 min: $\Delta pH_i$ was −0.052±0.006 (p<0.001, n=5) (FIG. 7B). This signifies inhibition of the transfected $Na^+/H^+$ exchanger. We have previously demonstrated that PMA does not cause acidification in PS120 cells outside of its inhibition of the $Na^+/H^+$ exchanger (29).

EXAMPLE 3

Northern blot analysis and tissue distribution of human NHE3 message

Figure 8:
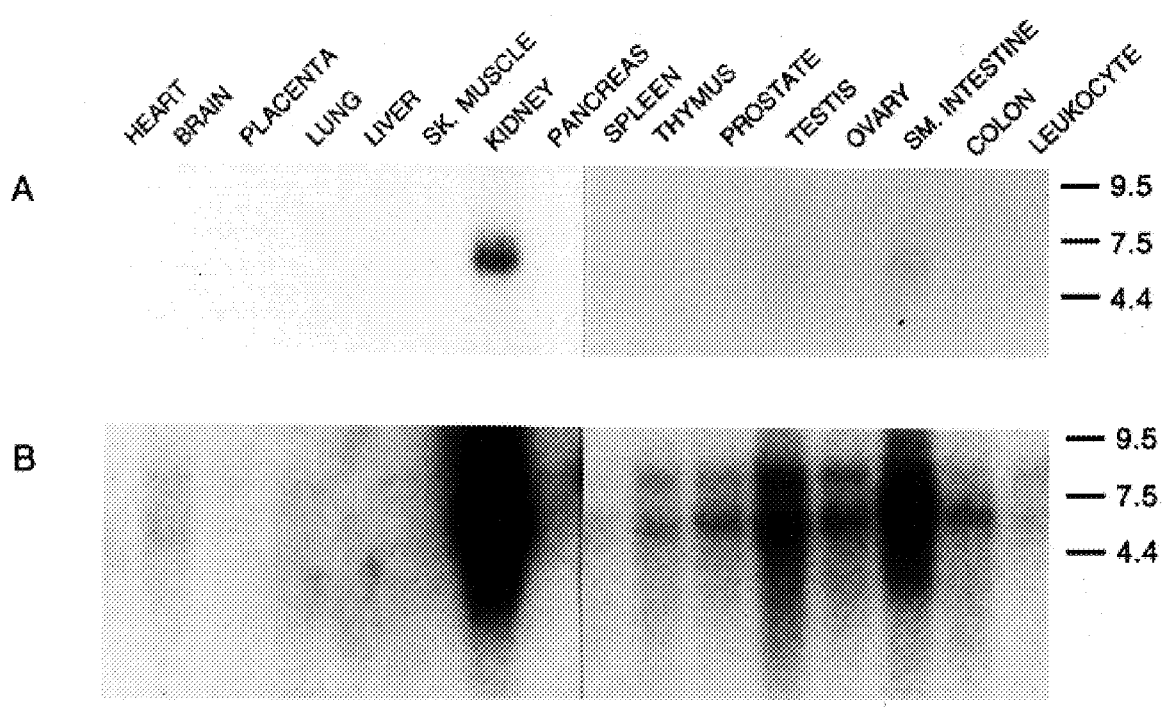
FIG. 8. This figure sets forth a northern blot analysis of expression of NHE3 in human tissues.

To determine the size of the human NHE3 message and to examine its expression in a variety of human tissues, we probed Northern blots of multiple human tissues (commercially prepared human Northern blots, Human MTN and Human MTN II, Clontech) with the 935 bp 5' SmaI fragment of clone HKC5 (FIG. 8).

Each lane contained 1 $\mu g$ of $poly(A)^+$ RNA from the indicated tissues. Both blots (left panel=MTN blot, right panel=MTN blot II) were probed in a single solution under high stringency conditions using the human NHE3 specific $^{32}P$ probe. The blots were washed together under high stringency conditions. Autoradiograms were exposed for two different time periods: A, 16 h; B, 7 days. RNA size standards (in kilobases) are shown on the right of the figures.

We used the cytoplasmic domain probe because homology in this region among NHE isoforms is low (47% nucleotide identity with NHE2, 41% with NHE1), minimizing possible cross hybridization with other NHE isoforms. Furthermore, we confirmed that this NHE3 probe did not hybridize to NHE1 or NHE2 by Southern blotting under high stringency hybridization conditions (data not shown).

At 16 h exposure of the autoradiogram (FIG. 8, panel A), a strong 6.7 kb band was detected in human kidney RNA, and a weaker 6.7 kb band was detected in the small intestine RNA, with two very weak bands detected in testes RNA, corresponding to 6.7 and 8.9 kb. Following a 7 day exposure, bands were detected in RNA from all tissues from the MTN II blot, and two additional tissues (brain and placenta) in the MTN blot (FIG. 8, panel B). The order of signal intensity for the various tissues was: kidney>>small intestine>>testes>ovary>colon=prostate>thymus>peripheral leukocyte=brain>spleen>placenta, and including endothelial cells. No message was detected in the heart, lung, liver, skeletal muscle, or pancreas. The bands in the kidney, small intestine and colon appeared to be made up almost entirely of the 6.7 kb size, whereas the 8.9 kb band seen in the other tissues were nearly as intense as the 6.7 kb band.

As NHE3 message in the rabbit and rat has only been detected in kidney, stomach, some intestinal tissues and brain (3,20,26), the finding that human NHE3 was present in these other tissues was unexpected. Consequently, we probed a newly obtained second MTN II blot, and the results from the first MTN II blot were confirmed. Furthermore, both MTN II blots were stripped and reprobed with a mouse protamine-1 cDNA (ATCC, Rockville, Md.) (33). The only hybridization signal present was that of the testicular specific 0.6 kb human protamine-1 message (8), seen only in the testes lanes, thus verifying the integrity and specificity of the MTN II blots' testes samples (results not shown).

REFERENCES

1. Aronson, P. S. Mechanisms of active $H^+$ secretion in the proximal tubule. *Am. J. Physiol.* 245: F647–F659, 1983.
2. Biemesderfer, D., J. Pizzonia, A. Abu-Alfa, M. Exner, R. Reilly, P. Igarashi, and P. S. Aronson. NHE3: a $Na^+/H^+$ exchanger isoform of renal brush border. *Am. J. Physiol.* F736–F742, 1993.
3. Bookstein, C., A. M. DePaoli, Y. Xie, P. Niu, M. W. Musch, M. C. Rao, and E. B. Chang. $Na^+/H^+$ exchangers, NHE-1 and NHE-3, of rat intestine: expression and localization. *J. Clin. Invest.* 93: 106–113, 1994.
4. Booth, I. W., G. Stange, H. Murer, T. R. Fenton, and P. J. Milla. Defective jejunal brush-border $Na^+/H^+$ exchange: A cause of congenital secretory diarrhoea. *Lancet* i: 1066–1069, 1985.
5. Borgese, F., C. Sardet, M. Cappadoro, J. Pouyssegur, and R. Motais. Cloning and expressing a cAMP-activated $Na^+/H^+$ exchanger: evidence that the cytopiasmic domain mediates hormonal regulation. *Proc. Natl. Acad. Sci. USA* 89: 6765–6769, 1992.
6. Brant, S. R., M. Bernstein, J. J. Wasmuth, B. W. Taylor, J. D. McPherson, X. Li, S. Walker, J. Pouyssegur, M. Donowitz, C. M. Tse, and E. W. Jabs. Physical and genetic mapping of a human apical epithelial $Na^+/H^+$ exchanger (NHE3) isoform to chromosome 5p15.3. *Genomics* 15: 668–672, 1993.
7. Counillon, L., A. Franchi, J. Pouyssegur. A point mutation of the $Na^+/H^+$ exchanger gene (NHE-1) and amplification of the mutated allele confer amiloride-resistance upon chronic acidosis. *Proc. Natl. Acad. Sci. USA* 90: 4508–4512, 1993.
8. Domenjoud, L., H. Kremling, P. Burfeind, W. M. Maier, and W. Engel. On the expression of protamine genes in the testis of man and other mammals. *Andrologia* 23: 333–337, 1991.
9. Hoogerwerf, W. A., C. Yun, S. Levine, J. L. M. Montgomery, A. J. Lazenby, C. M. Tse and M. Donowitz. Message distribution of three $Na/H^+$ exchangers along the rabbit ileal crypt-villus axis and demonstration that an epithelial isoform, NHE2, is present in ileal brush border membrane. *Gastroenterology* 106: A239 (Abstract), 1994.
10. Kleinman, J. G., J. M. Harig, J. A. Barry, K. Ramaswamy. $Na^+$ and $H^+$ transport in human jejunal brush-border membrane vesicles. *Am. J. Physiol.* 255: G206–G211, 1988.
11. Knickelbein, R. G., P. S. Aronson, W. Atherton, and J. W. Dobbins. Na and Cl transport across rabbit ileal brush border. I. Evidence for Na/H exchange. *Am. J. Physiol.* 245: G504–G510, 1983.
12. Knickelbein, R. G., P. S. Aronson, J. Seifter, C. M. Schron and J. W. Dobbins. Na and Cl transport across rabbit ileal brush border. II. Demonstration of $Cl/HCO_3$ exchange and mechanism for coupling. *Am. J. Physiol.* 249: G236–G249, 1985.
13. Kozak, M. An analysis of 5'-noncoding sequences from 699 vertebrate messenger RNAs. *Nucleic Acids Res.* 15: 8125–8148, 1987.
14. Levine, S., M. Montrose, C. M. Tse, and M. Donowitz. Kinetics and regulation of three cloned mammalian $Na^+/H^+$ exchangers stably expressed in a fibroblast cell line. *J. Biol. Chem.* 268: 25527–25535, 1993.
15. Lifton, R. P., C. Sardet, J. Pouyssegur, and J. M. Lalouel. Cloning of the human genomic amiloride-sensitive $Na^+/H^+$ antiporter gene, identification of genetic polymorphisms, and localization on the genetic map of chromosome 1p. *Genomics* 7:131–135, 1990.
16. Mahnensmith, R. L. and P. S. Aronson. The plasma membrane sodium-hydrogen exchanger and its role in physiological and pathophysiological processes. *Circ. Res.* 56:773–788, 1985.
17. McCombie, W. R., C. Heiner, J. M. Kelly, M. G. Fitzgerald, and J. D. Gocayne. Rapid and reliable fluorescent cycle sequencing of double stranded templates. *DNA Sequence* 2: 289–296, 1992.
18. Morduchowicz, G. A., D. Sheikh-Hamad, O. D. Jo, E. P. Nord, D. B. Lee, and N. Yanagawa. Increased $Na^+/H^+$ antiport activity in the renal brush border membrane of SHR. *Kidney Int.* 36:576–581, 1989.
19. Orlowski, J. Heterologous expression and functional properties of amiloride high affinity (NHE3) and low affinity (NHE3) isoforms of the rat $Na^+/H^+$ exchanger. *J. Biol. Chem.* 268: 16369–16377, 1993.
20. Orlowski, J., R. A. Kandasamy, and G. E. Shull. Molecular cloning of putative members of the $Na^+/H^+$ exchanger gene family. *J. Biol. Chem.* 267: 9331–9339, 1992.
21. Rood, R. P. and M. Donowitz. Regulation of small intestinal $Na^+$ absorption by protein kinases; implications for therapy of diarrheal diseases. *Viewpoints on Digestive Disease* 22: 1–6, 1990.
22. Sanger, F., S. Nicklen, and A. R. Coulson: DNA sequencing with chain-termination inhibitors. *Proc. Natl. Acad. Sci. USA* 74: 5463–5467, 1977.
23. Sardet, C., L. Counillon, A. Franchi, and J. Pouyssegur. Molecular cloning, primary structure and expression of the human growth factor-activatable $Na^+/H^+$ antiporter. *Cell* 56: 271–280, 1989.
24. Simchourtz, L., and E. J. Cragoe. Intracellular acidification-induced alkali metal cation $H^+$ exchange in human neutrophils. *J. Gen. Physiol.* 90: 737–762, 1987.
25. Smith, L. M., J. Z. Sanders, R. J. Kaiser, P. Hughes, C. Dodd, C. R. Connell, C. Heiner, S. B. H. Kent, and 25. L. E. Hood: Fluorescence detection in automated DNA sequence analysis. *Nature* 321; 674–679, 1986.
26. Tse, C. M., S. R. Brant, S. Walker, J. Pouyssegur, and M. Donowitz. Cloning and sequencing of a rabbit cDNA encoding an intestinal and kidney-specific $Na^+/H^+$ exchanger isoform (NHE-3). *J. Biol. Chem.* 267: 9340–9346, 1992.
27. Tse, C. M., S. Levine, C. H. C. Yun, S. R. Brant, L. Counillon, J. Pouyssegur, and M. Donowitz. Structure/function studies of the epithelial isoforms of the mammalian $Na^+/H^+$ exchanger gene family. *J. Membrane Biol.* 135: 93–108, 1993.
28. Tse, C. M., S. Levine, C. H. C. Yun, S. R. Brant, S. Nath, J. Pouyssegur, and M. Donowitz. Molecular properties, kinetics and regulation of mammalian $Na^+/H^+$ exchangers. *Cell Physiol. Biochem.* 4: 282–300, 1994.
29. Tse, C. M., S. A. Levine, C. H. C. Yun, S. R. Brant, J. Pouyssegur, M. H. Montrose, and M. Donowitz. Functional characteristics of a cloned epithelial $Na^+/H^+$ exchanger (NHE3): Resistance to amiloride and inhibition by protein kinase C. *Proc. Nat. Acad. Sci. USA* 90: 9110–9114, 1993.
30. Tse, C. M., S. A. Levine, C. H. C. Yun, M. H. Montrose, P. J. Little, J. Pouyssegur, and M. Donowitz. Cloning and expression of a rabbit cDNA encoding a serum-activated ethylisoprnpylamiloride-resistant epithelial $Na^+/H^+$ exchanger isoform NHE-2). *J. Biol. Chem.* 268: 11917–11924, 1993.
31. Tse, C. M., A. I. Ma, V. W. Yang, A. J. M. Watson, S. Levine M. H. Montrose, J. Potter, C. Sardet, J. Pouyssegur, and M. Donowitz. Molecular cloning and expression of a cDNA encoding the rabbit ileal villus cell basolateral membrane $Na^+/H^+$ exchanger. *EMBO J.* 10: 1957–1967, 1991.
32. Wakabayashi, S., P. Fafournoux, C. Sardet, and J. Pouyssegur: The $Na^+/H^+$ antiporter cytoplasmic domain mediates growth factor signals and controls $H^+$-sensing. *Proc. Natl. Acad. Sci. USA* 89: 2424–2428, 1992.
33. Yelick, P. C., R. Balhorn, P. A. Johnson, M. C. Corzett, J. A. Mazrimas, K. C. Kleene, and N. B. Hecht. Mouse protamine 2 is synthesized as a precursor whereas mouse protamine 1 is not. *Mol. Cell Biol.* 7: 2173–2179, 1987.
34. Yun, C. H., S. Gurubhagavatula, S. A. Levine, J. M. Montgomery, S. R. Brant, M. E. Cohen, J. Pouyssegur, C. M. Tse, and M. Donowitz. Glucocorticoid stimulation of ileal $Na^+$ absorptive cell brush border $Na^+/H^+$ exchange and association with an increase in message for NHE-3, an epithelial isoform $Na^+/H^+$ exchanger. *J. Biol. Chem.* 268:206–211, 1993.
35. Yun, C. H. C., P. J. Little, S. K. Nath, S. A. Levine, J. Pouyssegur, C. M. Tse and M. Donowitz. Leu143 in the putative fourth membrane spanning domain is critical for amiloride inhibition of an epithelial $Na^+/H^+$ exchanger isoform (NHE2) *Biochem. Biophys. Res. Comm.* 193: 532–539, 1993.
36. Zamir, Z., J. A. Barry, and K. Ramaswamy. Sodium transport in human intestinal basolateral membrane vesicles. *Gastroenterology* 103: 1817–1822, 1992.
37. Berschneider, H. M., M. R. Knowles, R. G. Azizkhan, R. C. Boucher, N. A. Tobey, R. C. Orlando, and D. W. Powell. Altered intestinal chloride transport in cystic fibrosis. *FASEB J.* 2: 2625–2629, 1988.
38. Donowitz, M. and M. J. Welsh. Regulation of mammalian small intestinal electrolyte secretion. *Physiology of the Gastrointestinal Tract*, Ed. L. R. Johnson, Raven Press 2d ed. 1988, Chapter 48, 1351–1388.
39. U.S. Pat. Nos. 4,683,195 and 4,683,202.
40. Acra, S. and F. K. Ghisan. Increased $Na^+/H^+$ exchange in jejunal brush border membrane vesicles of spontaneously hypertensive rats. *Gastroenterology* 101: 430–436, 1991.
41. Freiberg J. M., J. Kinsella, and B. Sacktor. Glucocorticoids increase the $Na^+/H^+$ exchange and decrease the $Na^+$ gradient dependent phosphate uptake systems in renal brush border membrane vesicles. *Proc. Natl. Acad. Sci. USA* 79: 683–712, 1982.
42. Harguindey, S. and E. J. Cragoe Jr. The $Na^+/H^+$ antiporter in oncology in the light of the spontaneous regression of cancer and cell metabolism. *Medical Hypothesis* 39: 229–237, 1992.
43. Tung, J. S., B. L. Daugherty, L. O'Neill, S. W. Law, J. Han and G. E. Mark. PCR amplification of specific sequences from a cDNA library in *PCR Technology: Principles and Applications of DNA Amplification.* Erlich, H. A., Ed., Stockton Press, New York, 1989.
44. Miller, R. T., L. Counillon, G. Pages, R. P. Lifton, C. Sarget, and J. Pouyssegur. Structure of the 5'-flanking regulatory region in gene for human growth factor-activatable $Na^+/H^+$ exchanger NHE-1. *J. Bio. Chem.* 266: 10813–10819, 1991.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. A method of identifying agents that affect human NHE3, comprising the steps of:
   a) obtaining DNA encoding all or a functional portion of human NHE3;
   b) introducing that DNA into a recipient host cell whereby the host cell can perform Na+/H+ exchange;
   c) applying agents to the host cell; and
   d) assessing whether the agents affect Na+/H+ exchange.

2. The method of claim 1 wherein the assessment is done with a study selected from the group consisting of Na+ uptake and Na+ dependent alkalization.

3. The method of claim 1 wherein the affect is the activation of Na+/H+ exchange activity.

4. The method of claim 1 wherein the affect is the inhibition of Na+/H+ exchange activity.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single (D) TOPOLOGY: linear (i i) MOLECULE TYPE: DNA (genomic)

(x i) SEQUENCE DESCRIPTION: SEQ ID NO:1:

GCGAATTCCA CACGGTACCC ACGAC 25

(2) INFORMATION FOR SEQ ID NO:2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:2:

ATGCGGTCGG CCGGGCTGAG C 21

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:3:

CATCTGGACC TGGAACACG 19

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:4:

CGTAGCTGAT GGCATCCTTC 20

(2) INFORMATION FOR SEQ ID NO:5:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:5:

ATGCGCGTCG GGCCCCGGCG CTGA 24

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:6:

ATGCGTGTCG GCTCCTGGAG CTGA 24

(2) INFORMATION FOR SEQ ID NO:7:

(i) SEQUENCE CHARACTERISTICS:
  (A) LENGTH: 10 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:7:

GCAGGCGGCA 10

(2) INFORMATION FOR SEQ ID NO:8:

(i) SEQUENCE CHARACTERISTICS:
  (A) LENGTH: 2574 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:8:

| | | | | | |
|---|---|---|---|---|---|
| ATGTGGGGAC | TCGGGGCCCG | GGGCCCCGAC | CGGGGGCTGC | TGCTGGCGCT | GGCGCTGGGC | 60 |
| GGGCTGGCGC | GGGCCGGGGG | CGTCGAGGTG | GAGCCCGGCG | GCGCGCACGG | CGAGAGCGGG | 120 |
| GGCTTCCAGG | TGGTCACCTT | CGAGTGGGCC | CACGTGCAGG | ATCCCTACGT | CATCGCGCTC | 180 |
| TGGATCCTCG | TGGCCAGCTT | GGCCAAGATC | GGGTTCCACC | TGTCCCACAA | GGTCACCAGC | 240 |
| GTGGTTCCCG | AGAGCGCCCT | GCTCATCGTG | CTGGGCCTGG | TGCTGGGCGG | CATCGTCTGG | 300 |
| GCGGCCGACC | ACATCGCGTC | CTTCACACTG | ACGCCCACCG | TCTTCTTCTT | CTACCTGCTG | 360 |
| CCCCCCATCG | TGCTGGACGC | CGGCTACTTC | ATGCCCAACC | GCCTCTTCTT | CGGCAACCTG | 420 |
| GGGACCATCC | TGTTGTACGC | CGTCGTGGGT | ACCGTGTGGA | ACGCGGCCAC | CACCGGGCTG | 480 |
| TCCCTCTACG | GCGTCTTCCT | CAGTGGGCTC | ATGGGCGACC | TGCAGATTGG | GCTGCTGGAC | 540 |
| TTCCTCCTGT | TTGGCAGCCT | CATGGCGGCT | GTGGACCCGG | TGGCCGTCCT | GGCCGTGTTT | 600 |
| GAGGAGGTCC | ATGTCAACGA | GGTCCTGTTC | ATCATCGTCT | TCGGGGAGTC | GCTGCTGAAC | 660 |
| GACGCAGTCA | CCGTGGTTCT | GTACAATGTG | TTTGAATCTT | TCGTGGCGCT | GGGAGGTGAC | 720 |
| AACGTGACTG | GCGTGGACTG | CGTGAAGGGC | ATAGTGTCCT | TCTTCGTGGT | GAGCCTGGGG | 780 |
| GGCACGCTGG | TGGGGGTGGT | CTTCGCCTTC | CTGCTGTCGC | TGGTGACGCG | CTTCACCAAG | 840 |
| CATGTGCGTA | TCATCGAGCC | CGGCTTCGTG | TTCATCATCT | CCTACCTGTC | CTACCTGACG | 900 |
| TCCGAGATGC | TGTCGCTGTC | GGCCATCCTC | GCCATCACCT | TCTGTGGCAT | CTGCTGTCAG | 960 |
| AAGTATGTGA | AGGCAACAT | CTCGGAGCAG | TCGGCCACCA | CCGTGCGCTA | CACCATGAAG | 1020 |
| ATGCTGGCCA | GCAGCGCCGA | GACCATCATC | TTCATGTTCC | TGGGTATCTC | GGCCGTGAAC | 1080 |
| CCGTTCATCT | GGACCTGGAA | CACGGCCTTC | GTGCTCCTGA | CGCTGGTCTT | CATCTCCGTG | 1140 |
| TACCGGGCCA | TCGGTGTGGT | CCTGCAGACC | TGGCTTCTGA | ACCGCTACCG | CATGGTGCAG | 1200 |
| CTGGAGCCCA | TTGACCAGGT | GGTCCTGTCC | TACGGGGCC | TGCGCGGGGC | CGTGGCCTTT | 1260 |
| GCCCTGGTGG | TGCTTCTGGA | TGGAGACAAG | GTCAAGGAGA | AGAACCTGTT | CGTCAGCACC | 1320 |
| ACCATCATCG | TAGTGTTGTT | CACCGTCATC | TTCCAGGGCC | TGACCATCAA | GCCTCTGGTG | 1380 |
| CAGTGGCTGA | AGGTGAAGAG | GAGCGAGCAC | CGGAACCTC | GGCTCAACGA | GAAGCTGCAC | 1440 |
| GGCCGCGCTT | TCGACCACAT | CCTCTCGGCC | ATCGAGGACA | TATCCGGACA | GATCGGGCAC | 1500 |

-continued

```
AATTATCTCA GAGACAAGTG GTCCCACTTC GACAGGAAGT TCCTCAGCAG GGTCCTCATG    1560
AGACGGTCGG CCCAGAAGTC TCGAGACCGG ATCCTGAATG TCTTCCACGA GCTGAACCTG    1620
AAGGATGCCA TCAGCTACGT GGCTGAGGGA GAGCGCCGCG GGTCCCTGGC CTTCATCCGC    1680
TCCCCCAGCA CCGACAACGT GGTCAACGTG GACTTCACGC CACGATCGTC CACCGTGGAG    1740
GCCTCTGTCT CCTACCTCCT GAGAGAAAAT GTCAGCGCTG TCTGCCTGGA CATGCAGTCT    1800
CTGGAGCAGC GACGGCGGAG CATCCGGGAC GCGGAGGACA TGGTCACGCA CCACACGCTA    1860
CAGCAGTACC TGTACAAGCC GCGGCAGGAG TACAAGCATC TGTACAGCCG ACACGAGCTC    1920
ACGCCCACGG AGGACGAGAA ACAGGACCGG GAAATCTTCC ACAGGACCAT GCGGAAGCGC    1980
CTGGAGTCCT TCAAGTCGAC CAAGCTGGGG CTCAACCAGA ACAAGAAGGC AGCCAAGCTG    2040
TACAAGCGGG AGCGTGCCCA GAAGCGGAGA AACAGCAGCA TCCCCAATGG GAAGCTGCCC    2100
ATGGAGAGCC CTGCGCAGAA TTTCACCATC AAGGAGAAAG ACTTGGAACT TTCAGACACC    2160
GAGGAGCCCC CCAACTATGA TGAGGAGATG AGTGGGGGGA TCGAGTTCCT GGCTAGTGTC    2220
ACCAAGGACA CAGCGTCCGA CTCCCCTGCA GGAATTGACA CCCTGTGTT TTCTCCGGAC     2280
GAGGCCCTGG ACCGCAGCCT CCTGGCCAGG CTGCCGCCCT GGCTGTCTCC CGGGGAGACG    2340
GTGGTCCCCT CGCAGAGGGC CCGCACGCAG ATTCCCTACT CTCCCGGCAC CTTCCGCCGC    2400
CTGATGCCCT TCCGCCTCAG CAGCAAGTCC GTGGACTCCT TCCTGCAGGC AGACGGCCCC    2460
GAGGAGCGGC CCCCCGCCGC CCTCCCCGAG TCCACACACA TGTGACACCG GCTCCGACAC    2520
GCCGCTAACC GGCCGCTCGT CCCCGCGCCA CGGTCCGCCC ACCGCCGCCG CCGC          2574
```

( 2 ) INFORMATION FOR SEQ ID NO:9:

( i ) SEQUENCE CHARACTERISTICS:
        ( A ) LENGTH: 834 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Met Trp Gly Leu Gly Ala Arg Gly Pro Asp Arg Gly Leu Leu Leu Ala
 1               5                  10                  15

Leu Ala Leu Gly Gly Leu Ala Arg Ala Gly Gly Val Glu Val Glu Pro
                20                  25                  30

Gly Gly Ala His Gly Glu Ser Gly Gly Phe Gln Val Val Thr Phe Glu
                35                  40                  45

Trp Ala His Val Gln Asp Pro Tyr Val Ile Ala Leu Trp Ile Leu Val
        50                  55                  60

Ala Ser Leu Ala Lys Ile Gly Phe His Leu Ser His Lys Val Thr Ser
65                  70                  75                  80

Val Val Pro Glu Ser Ala Leu Leu Ile Val Leu Gly Leu Val Leu Gly
                85                  90                  95

Gly Ile Val Trp Ala Ala Asp His Ile Ala Ser Phe Thr Leu Thr Pro
               100                 105                 110

Thr Val Phe Phe Phe Tyr Leu Leu Pro Pro Ile Val Leu Asp Ala Gly
           115                 120                 125

Tyr Phe Met Pro Asn Arg Leu Phe Phe Gly Asn Leu Gly Thr Ile Leu
       130                 135                 140

Leu Tyr Ala Val Val Gly Thr Val Trp Asn Ala Ala Thr Thr Gly Leu
145                 150                 155                 160
```

```
Ser  Leu  Tyr  Gly  Val  Phe  Leu  Ser  Gly  Leu  Met  Gly  Asp  Leu  Gln  Ile
               165                 170                      175

Gly  Leu  Leu  Asp  Phe  Leu  Leu  Phe  Gly  Ser  Leu  Met  Ala  Ala  Val  Asp
               180                 185                      190

Pro  Val  Ala  Val  Leu  Ala  Val  Phe  Glu  Glu  Val  His  Val  Asn  Glu  Val
          195                      200                 205

Leu  Phe  Ile  Ile  Val  Phe  Gly  Glu  Ser  Leu  Leu  Asn  Asp  Ala  Val  Thr
210                           215                      220

Val  Val  Leu  Tyr  Asn  Val  Phe  Glu  Ser  Phe  Val  Ala  Leu  Gly  Gly  Asp
225                      230                 235                           240

Asn  Val  Thr  Gly  Val  Asp  Cys  Val  Lys  Gly  Ile  Val  Ser  Phe  Phe  Val
               245                      250                      255

Val  Ser  Leu  Gly  Gly  Thr  Leu  Val  Gly  Val  Val  Phe  Ala  Phe  Leu  Leu
               260                      265                      270

Ser  Leu  Val  Thr  Arg  Phe  Thr  Lys  His  Val  Arg  Ile  Ile  Glu  Pro  Gly
               275                 280                      285

Phe  Val  Phe  Ile  Ile  Ser  Tyr  Leu  Ser  Tyr  Leu  Thr  Ser  Glu  Met  Leu
     290                      295                 300

Ser  Leu  Ser  Ala  Ile  Leu  Ala  Ile  Thr  Phe  Cys  Gly  Ile  Cys  Cys  Gln
305                      310                 315                           320

Lys  Tyr  Val  Lys  Ala  Asn  Ile  Ser  Glu  Gln  Ser  Ala  Thr  Thr  Val  Arg
               325                      330                      335

Tyr  Thr  Met  Lys  Met  Leu  Ala  Ser  Ser  Ala  Glu  Thr  Ile  Ile  Phe  Met
               340                      345                      350

Phe  Leu  Gly  Ile  Ser  Ala  Val  Asn  Pro  Phe  Ile  Trp  Thr  Trp  Asn  Thr
          355                      360                 365

Ala  Phe  Val  Leu  Leu  Thr  Leu  Val  Phe  Ile  Ser  Val  Tyr  Arg  Ala  Ile
370                           375                 380

Gly  Val  Val  Leu  Gln  Thr  Trp  Leu  Leu  Asn  Arg  Tyr  Arg  Met  Val  Gln
385                      390                      395                      400

Leu  Glu  Pro  Ile  Asp  Gln  Val  Val  Leu  Ser  Tyr  Gly  Gly  Leu  Arg  Gly
               405                      410                      415

Ala  Val  Ala  Phe  Ala  Leu  Val  Val  Leu  Asp  Gly  Asp  Lys  Val  Lys
               420                      425                 430

Glu  Lys  Asn  Leu  Phe  Val  Ser  Thr  Thr  Ile  Ile  Val  Val  Phe  Phe  Thr
          435                      440                      445

Val  Ile  Phe  Gln  Gly  Leu  Thr  Ile  Lys  Pro  Leu  Val  Gln  Trp  Leu  Lys
     450                      455                 460

Val  Lys  Arg  Ser  Glu  His  Arg  Glu  Pro  Arg  Leu  Asn  Glu  Lys  Leu  His
465                      470                 475                           480

Gly  Arg  Ala  Phe  Asp  His  Ile  Leu  Ser  Ala  Ile  Glu  Asp  Ile  Ser  Gly
               485                      490                      495

Gln  Ile  Gly  His  Asn  Tyr  Leu  Arg  Asp  Lys  Trp  Ser  His  Phe  Asp  Arg
               500                 505                      510

Lys  Phe  Leu  Ser  Arg  Val  Leu  Met  Arg  Arg  Ser  Ala  Gln  Lys  Ser  Arg
          515                 520                      525

Asp  Arg  Ile  Leu  Asn  Val  Phe  His  Glu  Leu  Asn  Leu  Lys  Asp  Ala  Ile
     530                      535                 540

Ser  Tyr  Val  Ala  Glu  Gly  Glu  Arg  Arg  Gly  Ser  Leu  Ala  Phe  Ile  Arg
545                      550                      555                      560

Ser  Pro  Ser  Thr  Asp  Asn  Val  Val  Asn  Val  Asp  Phe  Thr  Pro  Arg  Ser
               565                      570                      575

Ser  Thr  Val  Glu  Ala  Ser  Val  Ser  Tyr  Leu  Leu  Arg  Glu  Asn  Val  Ser
               580                      585                      590
```

| | | | | | | | | | | | | | | |
|---|---|---|---|---|---|---|---|---|---|---|---|---|---|---|
| Ala | Val | Cys<br>595 | Leu | Asp | Met | Gln | Ser<br>600 | Leu | Glu | Gln | Arg | Arg<br>605 | Ser | Ile |
| Arg | Asp<br>610 | Ala | Glu | Asp | Met | Val<br>615 | Thr | His | His | Thr | Leu<br>620 | Gln | Gln | Tyr | Leu |
| Tyr<br>625 | Lys | Pro | Arg | Gln | Glu<br>630 | Tyr | Lys | His | Leu | Tyr<br>635 | Ser | Arg | His | Glu | Leu<br>640 |
| Thr | Pro | Thr | Glu | Asp<br>645 | Glu | Lys | Gln | Asp | Arg<br>650 | Glu | Ile | Phe | His | Arg<br>655 | Thr |
| Met | Arg | Lys | Arg<br>660 | Leu | Glu | Ser | Phe | Lys<br>665 | Ser | Thr | Lys | Leu | Gly<br>670 | Leu | Asn |
| Gln | Asn | Lys<br>675 | Lys | Ala | Ala | Lys | Leu<br>680 | Tyr | Lys | Arg | Glu | Arg<br>685 | Ala | Gln | Lys |
| Arg | Arg<br>690 | Asn | Ser | Ser | Ile | Pro<br>695 | Asn | Gly | Lys | Leu | Pro<br>700 | Met | Glu | Ser | Pro |
| Ala<br>705 | Gln | Asn | Phe | Thr | Ile<br>710 | Lys | Glu | Lys | Asp | Leu<br>715 | Glu | Leu | Ser | Asp | Thr<br>720 |
| Glu | Glu | Pro | Pro | Asn<br>725 | Tyr | Asp | Glu | Glu | Met<br>730 | Ser | Gly | Gly | Ile | Glu<br>735 | Phe |
| Leu | Ala | Ser | Val<br>740 | Thr | Lys | Asp | Thr | Ala<br>745 | Ser | Asp | Ser | Pro | Ala<br>750 | Gly | Ile |
| Asp | Asn | Pro<br>755 | Val | Phe | Ser | Pro | Asp<br>760 | Glu | Ala | Leu | Asp | Arg<br>765 | Ser | Leu | Leu |
| Ala | Arg<br>770 | Leu | Pro | Pro | Trp | Leu<br>775 | Ser | Pro | Gly | Glu | Thr<br>780 | Val | Val | Pro | Ser |
| Gln<br>785 | Arg | Ala | Arg | Thr | Gln<br>790 | Ile | Pro | Tyr | Ser | Pro<br>795 | Gly | Thr | Phe | Arg | Arg<br>800 |
| Leu | Met | Pro | Phe | Arg<br>805 | Leu | Ser | Ser | Lys | Ser<br>810 | Val | Asp | Ser | Phe | Leu<br>815 | Gln |
| Ala | Asp | Gly | Pro<br>820 | Glu | Glu | Arg | Pro | Pro<br>825 | Ala | Ala | Leu | Pro<br>830 | Glu | Ser | Thr |
| His | Met | | | | | | | | | | | | | | |

(2) INFORMATION FOR SEQ ID NO:10:

(i) SEQUENCE CHARACTERISTICS:
        (A) LENGTH: 834 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

| | | | | | | | | | | | | | | | |
|---|---|---|---|---|---|---|---|---|---|---|---|---|---|---|---|
| Met<br>1 | Trp | Gly | Leu | Gly<br>5 | Ala | Arg | Gly | Pro | Asp<br>10 | Arg | Gly | Leu | Leu | Leu<br>15 | Ala |
| Leu | Ala | Leu | Gly<br>20 | Gly | Leu | Ala | Arg | Ala<br>25 | Gly | Gly | Val | Glu | Val<br>30 | Glu | Pro |
| Gly | Gly | Ala<br>35 | His | Gly | Glu | Ser | Gly<br>40 | Gly | Phe | Gln | Val | Val<br>45 | Thr | Phe | Glu |
| Trp | Ala<br>50 | His | Val | Gln | Asp | Pro<br>55 | Tyr | Val | Ile | Ala | Leu<br>60 | Trp | Ile | Leu | Val |
| Ala<br>65 | Ser | Leu | Ala | Lys | Ile<br>70 | Gly | Phe | His | Leu | Ser<br>75 | His | Lys | Val | Thr | Ser<br>80 |
| Val | Val | Pro | Glu | Ser<br>85 | Ala | Leu | Leu | Ile | Val<br>90 | Leu | Gly | Leu | Val | Leu<br>95 | Gly |
| Gly | Ile | Val | Trp | Ala | Ala | Asp | His | Ile | Ala | Ser | Phe | Thr | Leu | Thr | Pro |

-continued

|  |  |  |  |  | 100 |  |  |  | 105 |  |  |  | 110 |  |
|---|---|---|---|---|---|---|---|---|---|---|---|---|---|---|
| Thr | Val | Phe<br>115 | Phe | Phe | Tyr | Leu | Leu<br>120 | Pro | Pro | Ile | Val | Leu<br>125 | Asp | Ala | Gly |
| Tyr | Phe<br>130 | Met | Pro | Asn | Arg | Leu<br>135 | Phe | Phe | Gly | Asn | Leu<br>140 | Gly | Thr | Ile | Leu |
| Leu<br>145 | Tyr | Ala | Val | Val | Gly<br>150 | Thr | Val | Trp | Asn | Ala<br>155 | Ala | Thr | Thr | Gly | Leu<br>160 |
| Ser | Leu | Tyr | Gly | Val<br>165 | Phe | Leu | Ser | Gly | Leu<br>170 | Met | Gly | Asp | Leu | Gln<br>175 | Ile |
| Gly | Leu | Leu | Asp<br>180 | Phe | Leu | Leu | Phe | Gly<br>185 | Ser | Leu | Met | Ala | Ala<br>190 | Val | Asp |
| Pro | Val | Ala<br>195 | Val | Leu | Ala | Val | Phe<br>200 | Glu | Glu | Val | His | Val<br>205 | Asn | Glu | Val |
| Leu | Phe<br>210 | Ile | Ile | Val | Phe | Gly<br>215 | Glu | Ser | Leu | Leu | Asn<br>220 | Asp | Ala | Val | Thr |
| Val<br>225 | Val | Leu | Tyr | Asn | Val<br>230 | Phe | Glu | Ser | Phe | Val<br>235 | Ala | Leu | Gly | Gly | Asp<br>240 |
| Asn | Val | Thr | Gly | Val<br>245 | Asp | Cys | Val | Lys | Gly<br>250 | Ile | Val | Ser | Phe | Phe<br>255 | Val |
| Val | Ser | Leu | Gly<br>260 | Gly | Thr | Leu | Val | Gly<br>265 | Val | Val | Phe | Ala | Phe<br>270 | Leu | Leu |
| Ser | Leu | Val<br>275 | Thr | Arg | Phe | Thr | Lys<br>280 | His | Val | Arg | Ile | Ile<br>285 | Glu | Pro | Gly |
| Phe | Val<br>290 | Phe | Ile | Ile | Ser | Tyr<br>295 | Leu | Ser | Tyr | Leu | Thr<br>300 | Ser | Glu | Met | Leu |
| Ser<br>305 | Leu | Ser | Ala | Ile | Leu<br>310 | Ala | Ile | Thr | Phe | Cys<br>315 | Gly | Ile | Cys | Cys | Gln<br>320 |
| Lys | Tyr | Val | Lys | Ala<br>325 | Asn | Ile | Ser | Glu | Gln<br>330 | Ser | Ala | Thr | Thr | Val<br>335 | Arg |
| Tyr | Thr | Met | Lys<br>340 | Met | Leu | Ala | Ser | Ser<br>345 | Ala | Glu | Thr | Ile | Ile<br>350 | Phe | Met |
| Phe | Leu | Gly<br>355 | Ile | Ser | Ala | Val | Asn<br>360 | Pro | Phe | Ile | Trp | Thr<br>365 | Trp | Asn | Thr |
| Ala | Phe<br>370 | Val | Leu | Leu | Thr | Leu<br>375 | Val | Phe | Ile | Ser | Val<br>380 | Tyr | Arg | Ala | Ile |
| Gly<br>385 | Val | Val | Leu | Gln | Thr<br>390 | Trp | Leu | Leu | Asn | Arg<br>395 | Tyr | Arg | Met | Val | Gln<br>400 |
| Leu | Glu | Pro | Ile | Asp<br>405 | Gln | Val | Val | Leu | Ser<br>410 | Tyr | Gly | Gly | Leu | Arg<br>415 | Gly |
| Ala | Val | Ala | Phe<br>420 | Ala | Leu | Val | Val | Leu<br>425 | Leu | Asp | Gly | Asp | Lys<br>430 | Val | Lys |
| Glu | Lys | Asn<br>435 | Leu | Phe | Val | Ser | Thr<br>440 | Thr | Ile | Ile | Val | Val<br>445 | Phe | Phe | Thr |
| Val | Ile<br>450 | Phe | Gln | Gly | Leu | Thr<br>455 | Ile | Lys | Pro | Leu | Val<br>460 | Gln | Trp | Leu | Lys |
| Val<br>465 | Lys | Arg | Ser | Glu | His<br>470 | Arg | Glu | Pro | Arg | Leu<br>475 | Asn | Glu | Lys | Leu | His<br>480 |
| Gly | Arg | Ala | Phe | Asp<br>485 | His | Ile | Leu | Ser | Ala<br>490 | Ile | Glu | Asp | Ile | Ser<br>495 | Gly |
| Gln | Ile | Gly | His | Asn<br>500 | Tyr | Leu | Arg | Asp<br>505 | Lys | Trp | Ser | His | Phe<br>510 | Asp | Arg |
| Lys | Phe | Leu<br>515 | Ser | Arg | Val | Leu | Met<br>520 | Arg | Arg | Ser | Ala | Gln<br>525 | Lys | Ser | Arg |

| | | | | | | | | | | | | | |
|---|---|---|---|---|---|---|---|---|---|---|---|---|---|
| Asp | Arg 530 | Ile | Leu | Asn | Val | Phe 535 | His | Glu | Leu | Asn 540 | Lys | Asp | Ala | Ile |
| Ser 545 | Tyr | Val | Ala | Glu | Gly 550 | Glu | Arg | Arg | Gly 555 | Ser | Leu | Ala | Phe | Ile | Arg 560 |
| Ser | Pro | Ser | Thr | Asp 565 | Asn | Val | Val | Asn | Val 570 | Asp | Phe | Thr | Pro | Arg 575 | Ser |
| Ser | Thr | Val | Glu 580 | Ala | Ser | Val | Ser | Tyr 585 | Leu | Leu | Arg | Glu | Asn 590 | Val | Ser |
| Ala | Val | Cys 595 | Leu | Asp | Met | Gln | Ser 600 | Leu | Glu | Gln | Arg | Arg 605 | Arg | Ser | Ile |
| Arg | Asp 610 | Ala | Glu | Asp | Met | Val 615 | Thr | His | His | Thr | Leu 620 | Gln | Gln | Tyr | Leu |
| Tyr 625 | Lys | Pro | Arg | Gln | Glu 630 | Tyr | Lys | His | Leu | Tyr 635 | Ser | Arg | His | Glu | Leu 640 |
| Thr | Pro | Thr | Glu | Asp 645 | Glu | Lys | Gln | Asp | Arg 650 | Glu | Ile | Phe | His | Arg 655 | Thr |
| Met | Arg | Lys | Arg 660 | Leu | Glu | Ser | Phe | Lys 665 | Ser | Thr | Lys | Leu | Gly 670 | Leu | Asn |
| Gln | Asn | Lys 675 | Lys | Ala | Ala | Lys | Leu 680 | Tyr | Lys | Arg | Glu | Ala 685 | Gln | Lys |
| Arg | Arg 690 | Asn | Ser | Ser | Ile | Pro 695 | Asn | Gly | Lys | Leu | Pro 700 | Met | Glu | Ser | Pro |
| Ala 705 | Gln | Asn | Phe | Thr | Ile 710 | Lys | Glu | Lys | Asp | Leu 715 | Glu | Leu | Ser | Asp | Thr 720 |
| Glu | Glu | Pro | Pro | Asn 725 | Tyr | Asp | Glu | Glu | Met 730 | Ser | Gly | Gly | Ile | Glu 735 | Phe |
| Leu | Ala | Ser | Val 740 | Thr | Lys | Asp | Thr | Ala 745 | Ser | Asp | Ser | Pro | Ala 750 | Gly | Ile |
| Asp | Asn | Pro 755 | Val | Phe | Ser | Pro | Asp 760 | Glu | Ala | Leu | Asp | Arg 765 | Ser | Leu | Leu |
| Ala | Arg 770 | Leu | Pro | Pro | Trp | Leu 775 | Ser | Pro | Gly | Glu | Thr 780 | Val | Val | Pro | Ser |
| Gln 785 | Arg | Ala | Arg | Thr | Gln 790 | Ile | Pro | Tyr | Ser | Pro 795 | Gly | Thr | Phe | Arg | Arg 800 |
| Leu | Met | Pro | Phe | Arg 805 | Leu | Ser | Ser | Lys | Ser 810 | Val | Asp | Ser | Phe | Leu 815 | Gln |
| Ala | Asp | Gly | Pro 820 | Glu | Glu | Arg | Pro | Pro 825 | Ala | Ala | Leu | Pro | Glu 830 | Ser | Thr |
| His | Met |

( 2 ) INFORMATION FOR SEQ ID NO:11:

( i ) SEQUENCE CHARACTERISTICS:
        ( A ) LENGTH: 831 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

| | | | | | | | | | | | | | | |
|---|---|---|---|---|---|---|---|---|---|---|---|---|---|---|
| Met 1 | Trp | His | Pro | Ala 5 | Leu | Gly | Pro | Gly | Trp 10 | Lys | Pro | Leu | Leu | Ala 15 | Leu |
| Ala | Val | Ala | Val 20 | Thr | Ser | Leu | Arg | Gly 25 | Val | Arg | Gly | Ile | Glu 30 | Glu |
| Pro | Asn | Ser 35 | Gly | Gly | Ser | Phe | Gln 40 | Ile | Val | Thr | Phe | Lys 45 | Trp | His | His |

| | | | | | | | | | | | | | | |
|---|---|---|---|---|---|---|---|---|---|---|---|---|---|---|
| Val | Gln | Asp | Pro | Tyr | Ile | Ile | Ala | Leu | Trp | Ile | Leu | Val | Ala | Ser | Leu |
| | 50 | | | | | 55 | | | | | 60 | | | | |
| Ala | Lys | Ile | Val | Phe | His | Leu | Ser | His | Lys | Val | Thr | Ser | Val | Val | Pro |
| 65 | | | | | 70 | | | | | 75 | | | | | 80 |
| Glu | Ser | Ala | Leu | Leu | Ile | Val | Leu | Gly | Leu | Val | Leu | Gly | Gly | Ile | Val |
| | | | | 85 | | | | | 90 | | | | | 95 | |
| Trp | Ala | Ala | Asp | His | Ile | Ala | Ser | Phe | Thr | Leu | Thr | Pro | Thr | Leu | Phe |
| | | | | 100 | | | | | 105 | | | | 110 | | |
| Phe | Phe | Tyr | Leu | Leu | Pro | Pro | Ile | Val | Leu | Asp | Ala | Gly | Tyr | Phe | Met |
| | | | 115 | | | | | 120 | | | | | 125 | | |
| Pro | Asn | Arg | Leu | Phe | Phe | Gly | Asn | Leu | Gly | Thr | Ile | Leu | Leu | Tyr | Ala |
| | 130 | | | | | 135 | | | | | 140 | | | | |
| Val | Ile | Gly | Thr | Ile | Trp | Asn | Ala | Ala | Thr | Thr | Gly | Leu | Ser | Leu | Tyr |
| 145 | | | | | 150 | | | | | 155 | | | | | 160 |
| Gly | Val | Phe | Leu | Ser | Gly | Leu | Met | Gly | Glu | Leu | Lys | Ile | Gly | Leu | Leu |
| | | | | 165 | | | | | 170 | | | | | 175 | |
| Asp | Phe | Leu | Leu | Phe | Gly | Ser | Leu | Ile | Ala | Ala | Val | Asp | Pro | Val | Ala |
| | | | 180 | | | | | 185 | | | | | 190 | | |
| Val | Leu | Ala | Val | Phe | Glu | Glu | Val | His | Val | Asn | Glu | Val | Leu | Phe | Ile |
| | | 195 | | | | | 200 | | | | | 205 | | | |
| Ile | Val | Phe | Gly | Glu | Ser | Leu | Leu | Asn | Asp | Ala | Val | Thr | Val | Val | Leu |
| | 210 | | | | | 215 | | | | | 220 | | | | |
| Tyr | Asn | Val | Phe | Glu | Ser | Phe | Val | Thr | Leu | Gly | Gly | Asp | Ala | Val | Thr |
| 225 | | | | | 230 | | | | | 235 | | | | | 240 |
| Gly | Val | Asp | Cys | Val | Lys | Gly | Ile | Val | Ser | Phe | Phe | Val | Val | Ser | Leu |
| | | | | 245 | | | | | 250 | | | | | 255 | |
| Gly | Gly | Thr | Leu | Val | Gly | Val | Ile | Phe | Ala | Phe | Leu | Leu | Ser | Leu | Val |
| | | | 260 | | | | | 265 | | | | | 270 | | |
| Thr | Arg | Phe | Thr | Lys | His | Val | Arg | Ile | Ile | Glu | Pro | Gly | Phe | Val | Phe |
| | | 275 | | | | | 280 | | | | | 285 | | | |
| Val | Ile | Ser | Tyr | Leu | Ser | Tyr | Leu | Thr | Ser | Glu | Met | Leu | Ser | Leu | Ser |
| | 290 | | | | | 295 | | | | | 300 | | | | |
| Ala | Ile | Leu | Ala | Ile | Thr | Phe | Cys | Gly | Ile | Cys | Cys | Gln | Lys | Tyr | Val |
| 305 | | | | | 310 | | | | | 315 | | | | | 320 |
| Lys | Ala | Asn | Ile | Ser | Glu | Gln | Ser | Ala | Thr | Thr | Val | Arg | Tyr | Thr | Met |
| | | | | 325 | | | | | 330 | | | | | 335 | |
| Lys | Met | Leu | Ala | Ser | Gly | Ala | Glu | Thr | Ile | Ile | Phe | Met | Phe | Leu | Gly |
| | | | 340 | | | | | 345 | | | | | 350 | | |
| Ile | Ser | Ala | Val | Asp | Pro | Val | Ile | Trp | Thr | Trp | Asn | Thr | Ala | Phe | Val |
| | | 355 | | | | | 360 | | | | | 365 | | | |
| Leu | Leu | Thr | Leu | Val | Phe | Ile | Ser | Val | Tyr | Arg | Ala | Ile | Gly | Val | Val |
| | 370 | | | | | 375 | | | | | 380 | | | | |
| Leu | Gln | Thr | Trp | Ile | Leu | Asn | Arg | Tyr | Arg | Met | Val | Gln | Leu | Glu | Thr |
| 385 | | | | | 390 | | | | | 395 | | | | | 400 |
| Ile | Asp | Gln | Val | Val | Met | Ser | Tyr | Gly | Gly | Leu | Arg | Gly | Ala | Val | Ala |
| | | | | 405 | | | | | 410 | | | | | 415 | |
| Tyr | Ala | Leu | Val | Val | Leu | Leu | Asp | Glu | Lys | Lys | Val | Lys | Glu | Lys | Asn |
| | | | 420 | | | | | 425 | | | | | 430 | | |
| Leu | Phe | Val | Ser | Thr | Thr | Leu | Ile | Val | Val | Phe | Phe | Thr | Val | Ile | Phe |
| | | 435 | | | | | 440 | | | | | 445 | | | |
| Gln | Gly | Leu | Thr | Ile | Lys | Pro | Leu | Val | Gln | Trp | Leu | Lys | Val | Lys | Arg |
| | 450 | | | | | 455 | | | | | 460 | | | | |
| Ser | Glu | Gln | Arg | Glu | Pro | Lys | Leu | Asn | Glu | Lys | Leu | His | Gly | Arg | Ala |

|       |     |     |     |     |     |     |     |     |     |     |     |     |     |     |     |
|-------|-----|-----|-----|-----|-----|-----|-----|-----|-----|-----|-----|-----|-----|-----|-----|
| 465   |     |     |     |     | 470 |     |     |     |     | 475 |     |     |     |     | 480 |
| Phe   | Asp | His | Ile | Leu | Ser | Ala | Ile | Glu | Asp | Ile | Ser | Gly | Gln | Ile | Gly |
|       |     |     |     | 485 |     |     |     |     | 490 |     |     |     |     | 495 |     |
| His   | Asn | Tyr | Leu | Arg | Asp | Lys | Trp | Ser | Asn | Phe | Asp | Arg | Lys | Phe | Leu |
|       |     |     | 500 |     |     |     |     | 505 |     |     |     |     | 510 |     |     |
| Ser   | Lys | Val | Leu | Met | Arg | Arg | Ser | Ala | Gln | Lys | Ser | Arg | Asp | Arg | Ile |
|       |     | 515 |     |     |     |     | 520 |     |     |     |     | 525 |     |     |     |
| Leu   | Asn | Val | Phe | His | Glu | Leu | Asn | Leu | Lys | Asp | Ala | Ile | Ser | Tyr | Val |
|       | 530 |     |     |     |     | 535 |     |     |     |     | 540 |     |     |     |     |
| Ala   | Glu | Gly | Glu | Arg | Arg | Gly | Ser | Leu | Ala | Phe | Ile | Arg | Ser | Pro | Ser |
| 545   |     |     |     |     | 550 |     |     |     |     | 555 |     |     |     |     | 560 |
| Thr   | Asp | Asn | Met | Val | Asn | Val | Asp | Phe | Ser | Thr | Pro | Arg | Pro | Ser | Thr |
|       |     |     |     | 565 |     |     |     |     | 570 |     |     |     |     | 575 |     |
| Val   | Glu | Ala | Ser | Val | Ser | Tyr | Phe | Leu | Arg | Glu | Asn | Val | Ser | Ala | Val |
|       |     |     | 580 |     |     |     |     | 585 |     |     |     |     | 590 |     |     |
| Cys   | Leu | Asp | Met | Gln | Ser | Leu | Glu | Gln | Arg | Arg | Arg | Ser | Ile | Arg | Asp |
|       |     | 595 |     |     |     |     | 600 |     |     |     |     | 605 |     |     |     |
| Thr   | Glu | Asp | Met | Val | Thr | His | His | Thr | Leu | Gln | Gln | Tyr | Leu | Tyr | Lys |
|       | 610 |     |     |     |     | 615 |     |     |     |     | 620 |     |     |     |     |
| Pro   | Arg | Gln | Glu | Tyr | Lys | His | Leu | Tyr | Ser | Arg | His | Glu | Leu | Thr | Pro |
| 625   |     |     |     |     | 630 |     |     |     |     | 635 |     |     |     |     | 640 |
| Asn   | Glu | Asp | Glu | Lys | Gln | Asp | Lys | Glu | Ile | Phe | His | Arg | Thr | Met | Arg |
|       |     |     |     | 645 |     |     |     |     | 650 |     |     |     |     | 655 |     |
| Lys   | Arg | Leu | Glu | Ser | Phe | Lys | Ser | Ala | Lys | Leu | Gly | Ile | Asn | Gln | Asn |
|       |     |     | 660 |     |     |     |     | 665 |     |     |     |     | 670 |     |     |
| Lys   | Lys | Ala | Ala | Lys | Leu | Tyr | Lys | Arg | Glu | Arg | Ala | Gln | Lys | Arg | Arg |
|       |     | 675 |     |     |     |     | 680 |     |     |     |     | 685 |     |     |     |
| Asn   | Ser | Ser | Ile | Pro | Asn | Gly | Lys | Leu | Pro | Met | Glu | Asn | Leu | Ala | His |
|       | 690 |     |     |     |     | 695 |     |     |     |     | 700 |     |     |     |     |
| Asn   | Phe | Thr | Ile | Lys | Glu | Lys | Asp | Leu | Glu | Leu | Ser | Glu | Pro | Glu | Glu |
| 705   |     |     |     |     | 710 |     |     |     |     | 715 |     |     |     |     | 720 |
| Ala   | Thr | Asn | Tyr | Glu | Glu | Ile | Ser | Gly | Gly | Ile | Glu | Phe | Leu | Ala | Ser |
|       |     |     |     | 725 |     |     |     |     | 730 |     |     |     |     | 735 |     |
| Val   | Thr | Lys | Asp | Val | Ala | Ser | Asp | Ser | Gly | Ala | Gly | Ile | Asp | Asn | Pro |
|       |     |     | 740 |     |     |     |     | 745 |     |     |     |     | 750 |     |     |
| Val   | Phe | Ser | Pro | Asp | Glu | Asp | Leu | Asp | Pro | Ser | Ile | Leu | Ser | Arg | Val |
|       |     | 755 |     |     |     |     | 760 |     |     |     |     | 765 |     |     |     |
| Pro   | Pro | Trp | Leu | Ser | Pro | Gly | Glu | Thr | Val | Val | Pro | Ser | Gln | Arg | Ala |
|       | 770 |     |     |     |     | 775 |     |     |     |     | 780 |     |     |     |     |
| Arg   | Val | Gln | Ile | Pro | Asn | Ser | Pro | Ser | Asn | Phe | Arg | Arg | Leu | Thr | Pro |
| 785   |     |     |     |     | 790 |     |     |     |     | 795 |     |     |     |     | 800 |
| Phe   | Arg | Leu | Ser | Asn | Lys | Ser | Val | Asp | Ser | Phe | Leu | Gln | Ala | Asp | Gly |
|       |     |     |     | 805 |     |     |     |     | 810 |     |     |     |     | 815 |     |
| Pro   | Glu | Glu | Gln | Leu | Gln | Pro | Ala | Ser | Pro | Glu | Ser | Thr | His | Met |     |
|       |     |     | 820 |     |     |     |     | 825 |     |     |     |     | 830 |     |     |

( 2 ) INFORMATION FOR SEQ ID NO:12:

( i ) SEQUENCE CHARACTERISTICS:
        ( A ) LENGTH: 832 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Met  Ser  Gly  Arg  Gly  Gly  Cys  Gly  Pro  Cys  Trp  Gly  Leu  Leu  Leu  Ala
1              5                        10                       15

Leu  Val  Leu  Ala  Leu  Gly  Ala  Leu  Pro  Trp  Thr  Gln  Gly  Ala  Glu  Gln
               20                  25                       30

Glu  His  His  Asp  Glu  Ile  Gln  Gly  Phe  Gln  Ile  Val  Thr  Phe  Lys  Trp
          35                  40                       45

His  His  Val  Gln  Asp  Pro  Tyr  Ile  Ile  Ala  Leu  Trp  Val  Leu  Val  Ala
     50                  55                       60

Ser  Leu  Ala  Lys  Ile  Val  Phe  His  Leu  Ser  His  Lys  Val  Thr  Ser  Val
65                       70                  75                            80

Val  Pro  Glu  Ser  Ala  Leu  Leu  Ile  Val  Leu  Gly  Leu  Val  Leu  Gly  Gly
                    85                       90                            95

Ile  Val  Leu  Ala  Ala  Asp  His  Ile  Ala  Ser  Phe  Thr  Leu  Thr  Pro  Thr
                    100                 105                      110

Val  Phe  Phe  Phe  Tyr  Leu  Leu  Pro  Pro  Ile  Val  Leu  Asp  Ala  Gly  Tyr
          115                      120                      125

Phe  Met  Pro  Asn  Arg  Leu  Phe  Phe  Ser  Asn  Leu  Gly  Ser  Ile  Leu  Leu
     130                      135                 140

Tyr  Ala  Val  Val  Gly  Thr  Val  Trp  Asn  Ala  Ala  Thr  Thr  Gly  Leu  Ser
145                      150                 155                           160

Leu  Tyr  Gly  Val  Phe  Leu  Ser  Gly  Ile  Met  Gly  Glu  Leu  Lys  Ile  Gly
                    165                      170                      175

Leu  Leu  Asp  Phe  Leu  Leu  Phe  Gly  Ser  Leu  Ile  Ala  Ala  Val  Asp  Pro
               180                      185                      190

Val  Ala  Val  Leu  Ala  Val  Phe  Glu  Glu  Val  His  Val  Asn  Glu  Val  Leu
          195                      200                 205

Phe  Ile  Ile  Val  Phe  Gly  Glu  Ser  Leu  Leu  Asn  Asp  Ala  Val  Thr  Val
     210                      215                 220

Val  Leu  Tyr  Asn  Val  Phe  Gln  Ser  Phe  Val  Thr  Leu  Gly  Gly  Asp  Lys
225                      230                 235                           240

Val  Thr  Gly  Val  Asp  Cys  Val  Lys  Gly  Ile  Val  Ser  Phe  Phe  Val  Val
                    245                      250                      255

Ser  Leu  Gly  Gly  Thr  Leu  Val  Gly  Val  Val  Phe  Ala  Phe  Leu  Leu  Ser
               260                      265                      270

Leu  Val  Thr  Arg  Phe  Thr  Lys  His  Val  Arg  Val  Ile  Glu  Pro  Gly  Phe
          275                      280                      285

Val  Phe  Ile  Ile  Ser  Tyr  Leu  Ser  Tyr  Leu  Thr  Ser  Glu  Met  Leu  Ser
     290                      295                 300

Leu  Ser  Ser  Ile  Leu  Ala  Ile  Thr  Phe  Cys  Gly  Ile  Cys  Cys  Gln  Lys
305                      310                 315                           320

Tyr  Val  Lys  Ala  Asn  Ile  Ser  Glu  Gln  Ser  Ala  Thr  Thr  Val  Arg  Tyr
                    325                 330                            335

Thr  Met  Lys  Met  Leu  Ala  Ser  Gly  Ala  Glu  Thr  Ile  Ile  Phe  Met  Phe
               340                 345                            350

Leu  Gly  Ile  Ser  Ala  Val  Asp  Pro  Leu  Ile  Trp  Thr  Trp  Asn  Thr  Ala
          355                 360                      365

Phe  Val  Arg  Leu  Thr  Leu  Leu  Phe  Val  Ser  Val  Phe  Arg  Ala  Ile  Gly
     370                 375                      380

Val  Val  Leu  Gln  Thr  Trp  Leu  Leu  Asn  Arg  Tyr  Arg  Met  Val  Gln  Leu
385                 390                      395                           400

Glu  Leu  Ile  Asp  Gln  Val  Val  Met  Ser  Tyr  Gly  Gly  Leu  Arg  Gly  Ala
               405                      410                      415

Val  Ala  Phe  Ala  Leu  Val  Ala  Leu  Leu  Asp  Gly  Asn  Lys  Val  Lys  Glu
```

-continued

|     |     |     |     | 420 |     |     |     | 425 |     |     |     | 430 |     |     |
|-----|-----|-----|-----|-----|-----|-----|-----|-----|-----|-----|-----|-----|-----|-----|
| Lys | Asn | Leu | Phe | Val | Ser | Thr | Thr | Ile | Ile | Val | Val | Phe | Thr | Val |
|     |     |     | 435 |     |     |     | 440 |     |     |     | 445 |     |     |     |
| Ile | Phe | Gln | Gly | Leu | Thr | Ile | Lys | Pro | Leu | Val | Gln | Trp | Leu | Lys | Val |
|     |     |     | 450 |     |     |     | 455 |     |     |     | 460 |     |     |     |
| Lys | Arg | Ser | Glu | His | Arg | Glu | Pro | Lys | Leu | Asn | Glu | Lys | Leu | His | Gly |
| 465 |     |     |     |     | 470 |     |     |     | 475 |     |     |     |     | 480 |
| Arg | Ala | Phe | Asp | His | Ile | Leu | Ser | Ala | Ile | Glu | Asp | Ile | Ser | Gly | Gln |
|     |     |     |     | 485 |     |     |     | 490 |     |     |     |     | 495 |     |
| Ile | Gly | His | Asn | Tyr | Leu | Arg | Asp | Lys | Trp | Ala | Asn | Phe | Asp | Arg | Arg |
|     |     |     | 500 |     |     |     | 505 |     |     |     |     | 510 |     |     |
| Phe | Leu | Ser | Lys | Leu | Leu | Met | Arg | Gln | Ser | Ala | Gln | Lys | Ser | Arg | Asp |
|     |     | 515 |     |     |     | 520 |     |     |     |     | 525 |     |     |     |
| Arg | Ile | Leu | Asn | Val | Phe | His | Glu | Leu | Asn | Leu | Lys | Asp | Ala | Ile | Ser |
|     | 530 |     |     |     |     | 535 |     |     |     |     | 540 |     |     |     |
| Tyr | Val | Thr | Glu | Gly | Glu | Arg | Arg | Gly | Ser | Leu | Ala | Phe | Ile | Arg | Ser |
| 545 |     |     |     |     | 550 |     |     |     | 555 |     |     |     |     | 560 |
| Pro | Ser | Thr | Asp | Asn | Met | Val | Asn | Val | Asp | Phe | Ser | Thr | Pro | Arg | Pro |
|     |     |     |     | 565 |     |     |     | 570 |     |     |     |     | 575 |     |
| Ser | Thr | Val | Glu | Ala | Ser | Val | Ser | Tyr | Leu | Leu | Arg | Glu | Ser | Ala | Ser |
|     |     |     | 580 |     |     |     | 585 |     |     |     |     | 590 |     |     |
| Ala | Val | Cys | Leu | Asp | Met | Gln | Ser | Leu | Glu | Gln | Arg | Arg | Arg | Ser | Val |
|     |     | 595 |     |     |     | 600 |     |     |     |     | 605 |     |     |     |
| Arg | Asp | Ala | Glu | Asp | Val | Ile | Thr | His | His | Thr | Leu | Gln | Gln | Tyr | Leu |
|     | 610 |     |     |     |     | 615 |     |     |     |     | 620 |     |     |     |
| Tyr | Lys | Pro | Arg | Gln | Glu | Tyr | Lys | His | Leu | Tyr | Ser | Arg | His | Val | Leu |
| 625 |     |     |     |     | 630 |     |     |     |     | 635 |     |     |     | 640 |
| Ser | Pro | Ser | Glu | Asp | Glu | Lys | Gln | Asp | Lys | Glu | Ile | Phe | His | Arg | Thr |
|     |     |     |     | 645 |     |     |     | 650 |     |     |     |     | 655 |     |
| Met | Arg | Lys | Arg | Leu | Glu | Ser | Phe | Lys | Ser | Ala | Lys | Leu | Gly | Leu | Gly |
|     |     |     | 660 |     |     |     | 665 |     |     |     |     | 670 |     |     |
| Gln | Ser | Lys | Lys | Ala | Thr | Lys | His | Lys | Arg | Glu | Arg | Glu | Arg | Ala | Gln |
|     |     | 675 |     |     |     | 680 |     |     |     |     | 685 |     |     |     |
| Lys | Arg | Arg | Asn | Ser | Ser | Val | Pro | Asn | Gly | Lys | Leu | Pro | Leu | Asp | Ser |
|     | 690 |     |     |     |     | 695 |     |     |     |     | 700 |     |     |     |
| Pro | Arg | Tyr | Gly | Leu | Thr | Leu | Lys | Glu | Arg | Glu | Leu | Glu | Leu | Ser | Asp |
| 705 |     |     |     |     | 710 |     |     |     |     | 715 |     |     |     | 720 |
| Pro | Glu | Glu | Ala | Pro | Asp | Tyr | Tyr | Glu | Ala | Glu | Lys | Met | Ser | Gly | Gly |
|     |     |     |     | 725 |     |     |     | 730 |     |     |     |     | 735 |     |
| Ile | Glu | Phe | Leu | Ala | Ser | Val | Thr | Lys | Val | Ser | Thr | Ser | Asp | Ser | Pro |
|     |     |     | 740 |     |     |     | 745 |     |     |     |     | 750 |     |     |
| Ala | Gly | Ile | Asp | Asn | Pro | Val | Phe | Ser | Pro | Asp | Glu | Asp | Leu | Ala | Pro |
|     |     | 755 |     |     |     | 760 |     |     |     |     | 765 |     |     |     |
| Ser | Leu | Leu | Ala | Arg | Val | Pro | Pro | Trp | Leu | Ser | Pro | Gly | Glu | Ala | Val |
|     | 770 |     |     |     |     | 775 |     |     |     | 780 |     |     |     |     |
| Val | Pro | Ser | Gln | Arg | Ala | Arg | Val | Gln | Ile | Pro | Tyr | Ser | Pro | Gly | Asn |
| 785 |     |     |     |     | 790 |     |     |     |     | 795 |     |     |     | 800 |
| Phe | Arg | Arg | Leu | Ala | Pro | Phe | Arg | Leu | Ser | Asn | Lys | Ser | Val | Asp | Ser |
|     |     |     |     | 805 |     |     |     | 810 |     |     |     |     | 815 |     |
| Phe | Leu | Leu | Ala | Glu | Asp | Gly | Ala | Glu | His | Pro | Glu | Ser | Thr | His | Met |
|     |     |     | 820 |     |     |     | 825 |     |     |     | 830 |     |     |     |